US007981676B2

(12) United States Patent (10) Patent No.: US 7,981,676 B2
Boehm et al. (45) Date of Patent: *Jul. 19, 2011

(54) METHOD FOR TRANSFER OF MOLECULAR SUBSTANCES WITH PROKARYOTIC NUCLEIC ACID-BINDING PROTEINS

(75) Inventors: Gerald Boehm, Halle (DE); Dirk Esser, Cambridge (GB)

(73) Assignee: ACGT Progenomics AG, Halle (DE)

( * ) Notice: Subject to any disclaimer, the term of this patent is extended or adjusted under 35 U.S.C. 154(b) by 3 days.

This patent is subject to a terminal disclaimer.

(21) Appl. No.: 12/207,467

(22) Filed: Sep. 9, 2008

(65) Prior Publication Data

US 2009/0155912 A1 Jun. 18, 2009

Related U.S. Application Data

(63) Continuation of application No. 10/954,549, filed on Sep. 29, 2004, now Pat. No. 7,435,595, which is a continuation of application No. 10/129,393, filed as application No. PCT/EP00/10875 on Nov. 3, 2000, now abandoned.

(30) Foreign Application Priority Data

Nov. 3, 1999 (DE) .................................... 19952983

(51) Int. Cl.
*C12N 15/00* (2006.01)
(52) U.S. Cl. ......................... 435/455; 435/456; 435/458
(58) Field of Classification Search .................... None
See application file for complete search history.

(56) References Cited

U.S. PATENT DOCUMENTS

| 4,179,337 | A | 12/1979 | Davis et al. | |
|---|---|---|---|---|
| 5,888,732 | A | 3/1999 | Hartley et al. | |
| 5,965,404 | A | 10/1999 | Buschle et al. | |
| 7,435,595 | B2 * | 10/2008 | Boehm et al. | 435/455 |

FOREIGN PATENT DOCUMENTS

EP 0 908 521 A1 4/1999

OTHER PUBLICATIONS

Bian, J. et al. "Nuclear Translocation of HIV-1 Matrix Protein P17: The Use of *Aequora victoria* Green Fluorescence Protein in Protein Tagging and Tracing," *Protein Studies Program, Oklahoma Medical Research Foundation*, Univ. of Okla. *Health Sci. Ctr.* Oklahoma City. OK 73104 1995, 1 page total (abstract).
Boulikas, T. and Martin, F. "Histones, Protamine, and Polylysine but not Poly(E:K) Enhance Transfection Efficiency," *International J. of Oncology* 1997, pp. 317-322, vol. 10.
Branden, L.J. et al., "A Peptide Nucleic Acid-nuclear Localization Signal Fusion that Mediates Nuclear Transport of DNA," *Nature Biotechnology* Aug. 1999, pp. 784-787, vol. 17.
Elliott, G and O'Hare, P. "Intercellular Trafficking and Protein Delivery by a Herpesvirus Structural Protein," *Cell* Jan. 24, 1997, pp. 223-233, vol. 88.
Esser, D. et al. "A Hyperthermostable Bacterial Histone-like Protein as an Efficient Mediator for Transfection of Eukaryotic Cells," *Nature Biotechnology* Nov. 2000, pp. 1211-1213, vol. 18.
Esser, D. et al. "The HU Protein from Thermotoga maritima: Recombinant Expression, Purification and Physicochemical Characterization of an Extremely Hyperthermophilic DNA-binding Protein," *J. Mol. Biol.* 1999, pp. 1135-1146, vol. 291.
Fritz, D. et al. "Gene Transfer into Mammalian Cells Using Histone-Condensed Plasmid DNA," *Human Gene Therapy* Aug. 1996, pp. 1395-1404, vol. 7.
Hentschel, C.C. and Birnsteil, M.L. "The Organization and Expression of Histone Gene Families," *Cell* 1981, pp. 301-313, vol. 25, No. 2.
Ledley, F.D.; "Nonviral gene therapy: the promise of genes as pharmaceutical products"; 1995, *Hum. Gene Ther*. (Abstract), vol. 6, No. 9, pp. 1129-1144.
Li, J.Y. et al.: "Histones and histone-like DNA-binding proteins: correlations between structural differences, properties and functions"; 1999, *Microbiology*, vol. 145, pp. 1-3.
Ziemienowicz, A. et al. "Import of DNA into Mammalian Nuclei by Proteins Originating from a Plant Pathogenic Bacterium," *Proc. Natl. Acad. Sci USA* Mar. 1999, pp. 3729-3733, vol. 96.

* cited by examiner

*Primary Examiner* — James S Ketter
(74) *Attorney, Agent, or Firm* — Kilpatrick Townsend & Stockton LLP

(57) ABSTRACT

The invention relates to a method for the transfer of molecular substances, for example proteins or nucleic acids in cells, in the case of using DNA combined with a possible gene expression. A prokaryotic nucleic acid-binding protein is used for the transfer, which is preferably obtained from a thermostable organism. Where the substance to be transferred is a nucleic acid, the protein forms a reversible complex with the nucleic acid. The prokaryotic protein condenses and compacts the nucleic acids. Said nucleic acids can be taken up in the target cells after suitable incubation.

8 Claims, 10 Drawing Sheets

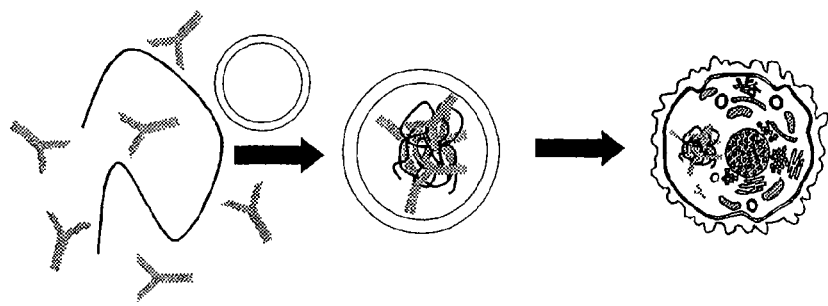
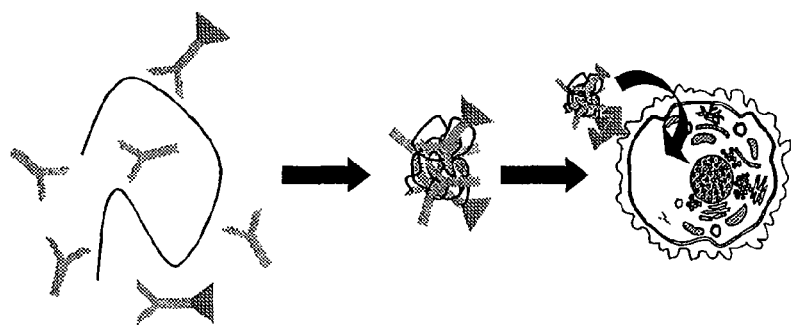
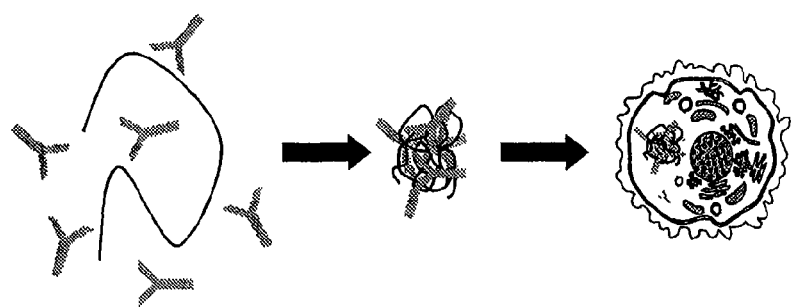
Figure 1. Schematic representation of the present invention.

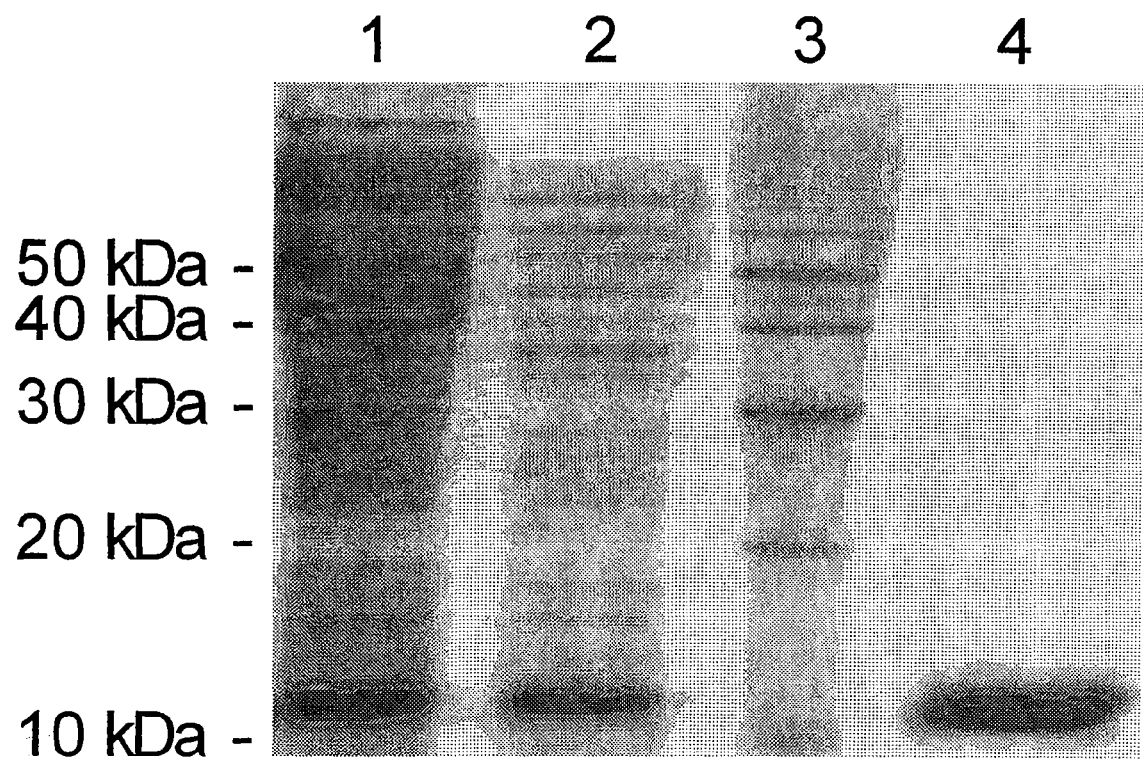
Figure 2: SDS PAGE for the analysis of the purification of TmHU.

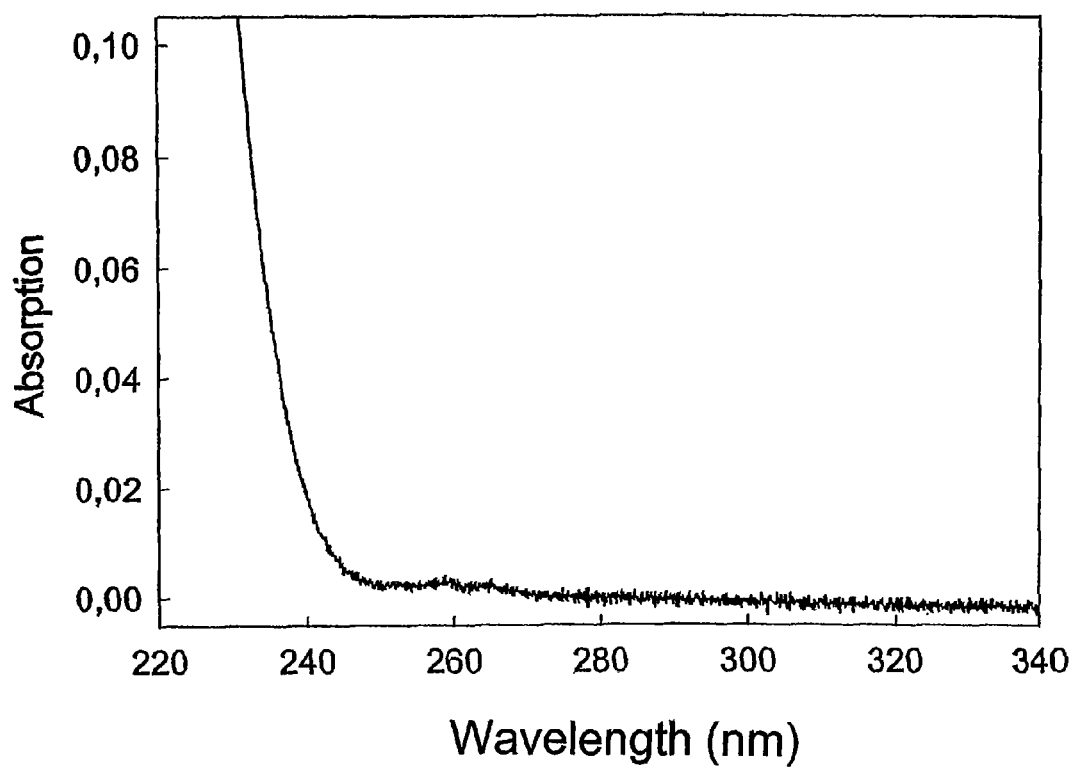
Figure 3: Spectroscopic characterization of native and purified TmHU.

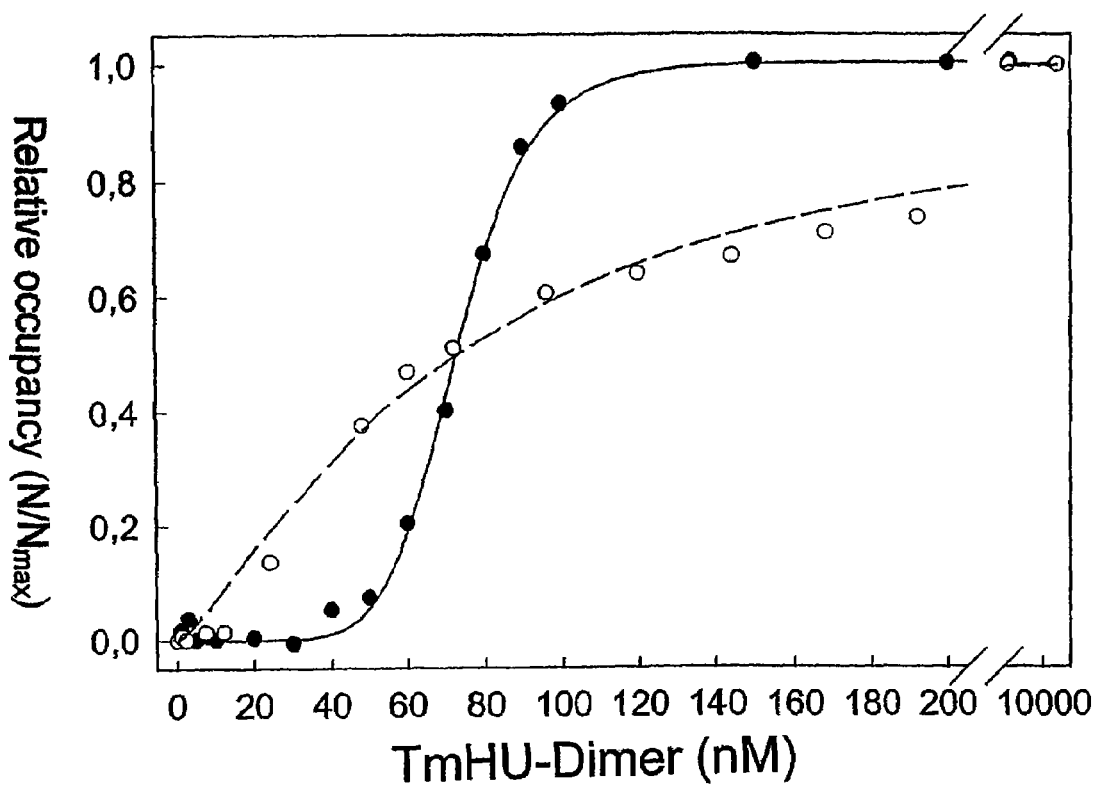
Figure 4. Measurement of the TmHU binding to DNA fragments of different sizes.

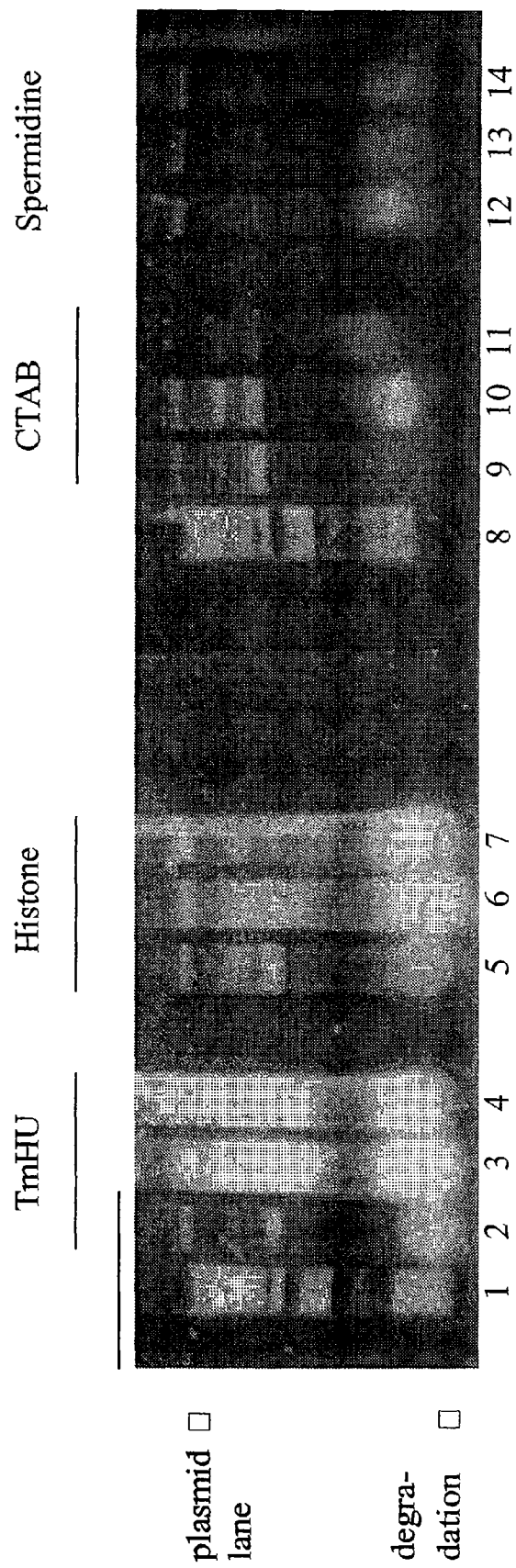
Figure 5. Protection of a model DNA from degradation by nucleases.

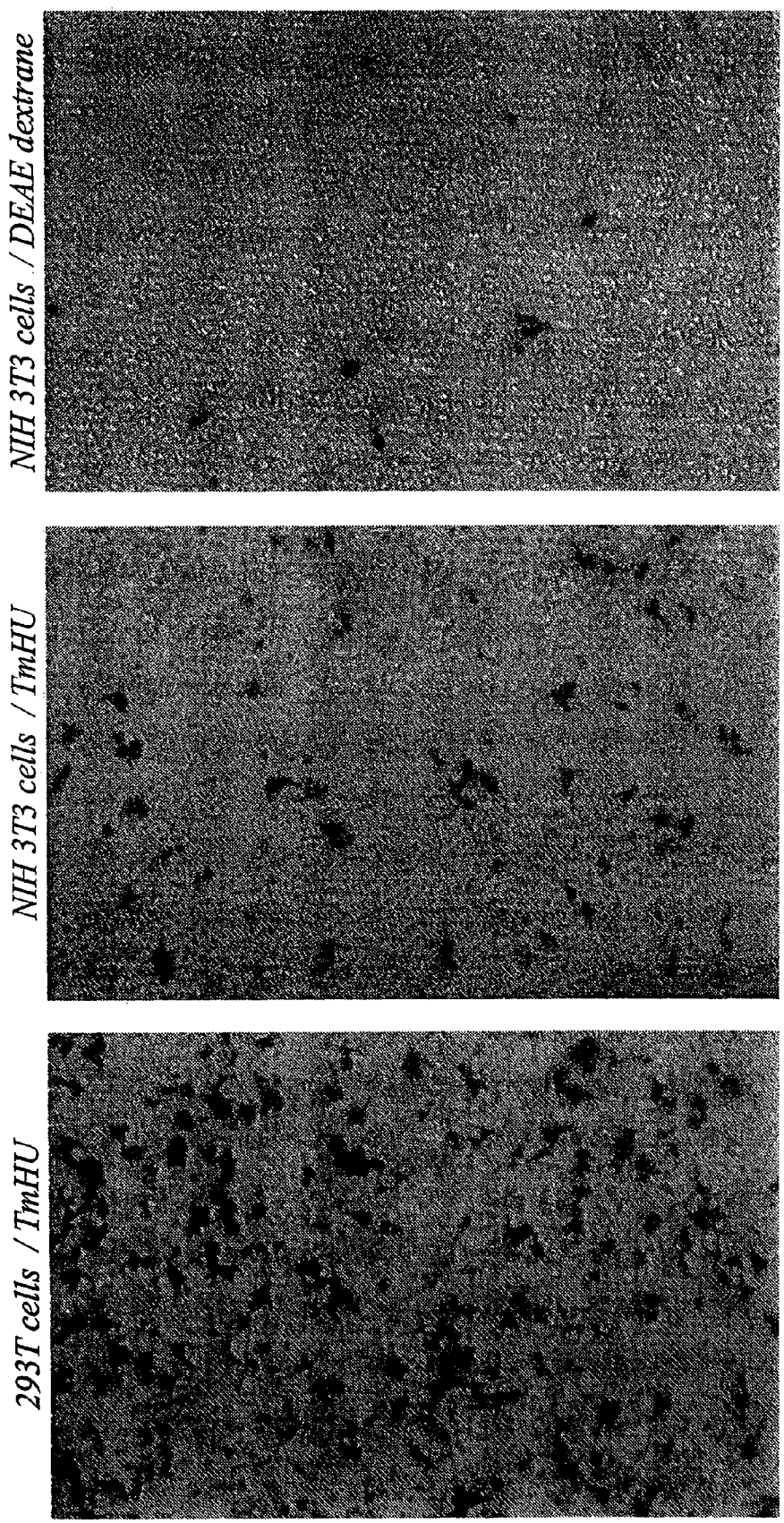
Figure 6. Transfection efficiency of TmHU.

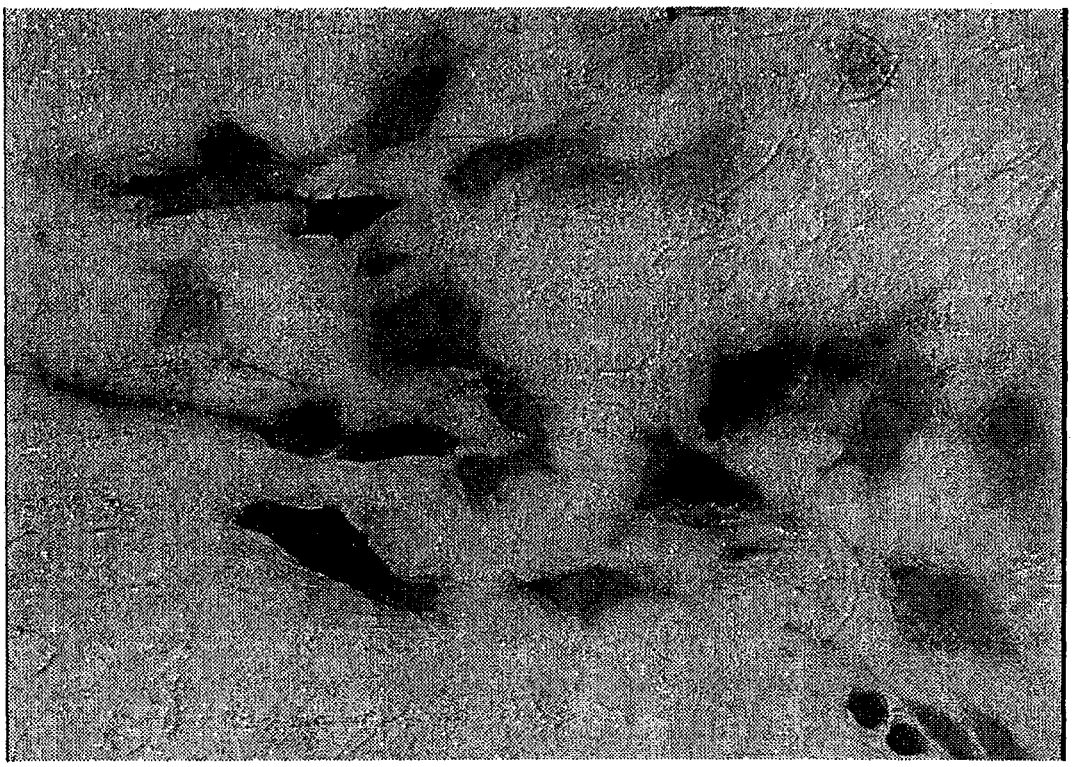
Figure 7. Transfection of cells.

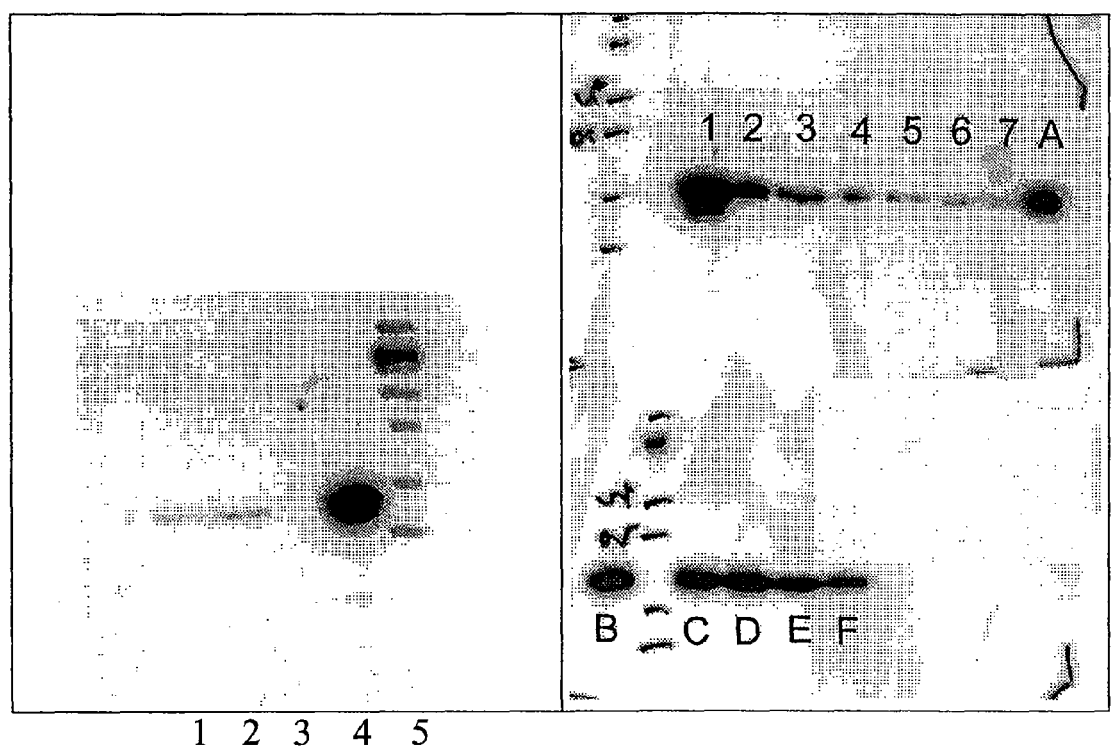
Figure 8. Western blots.

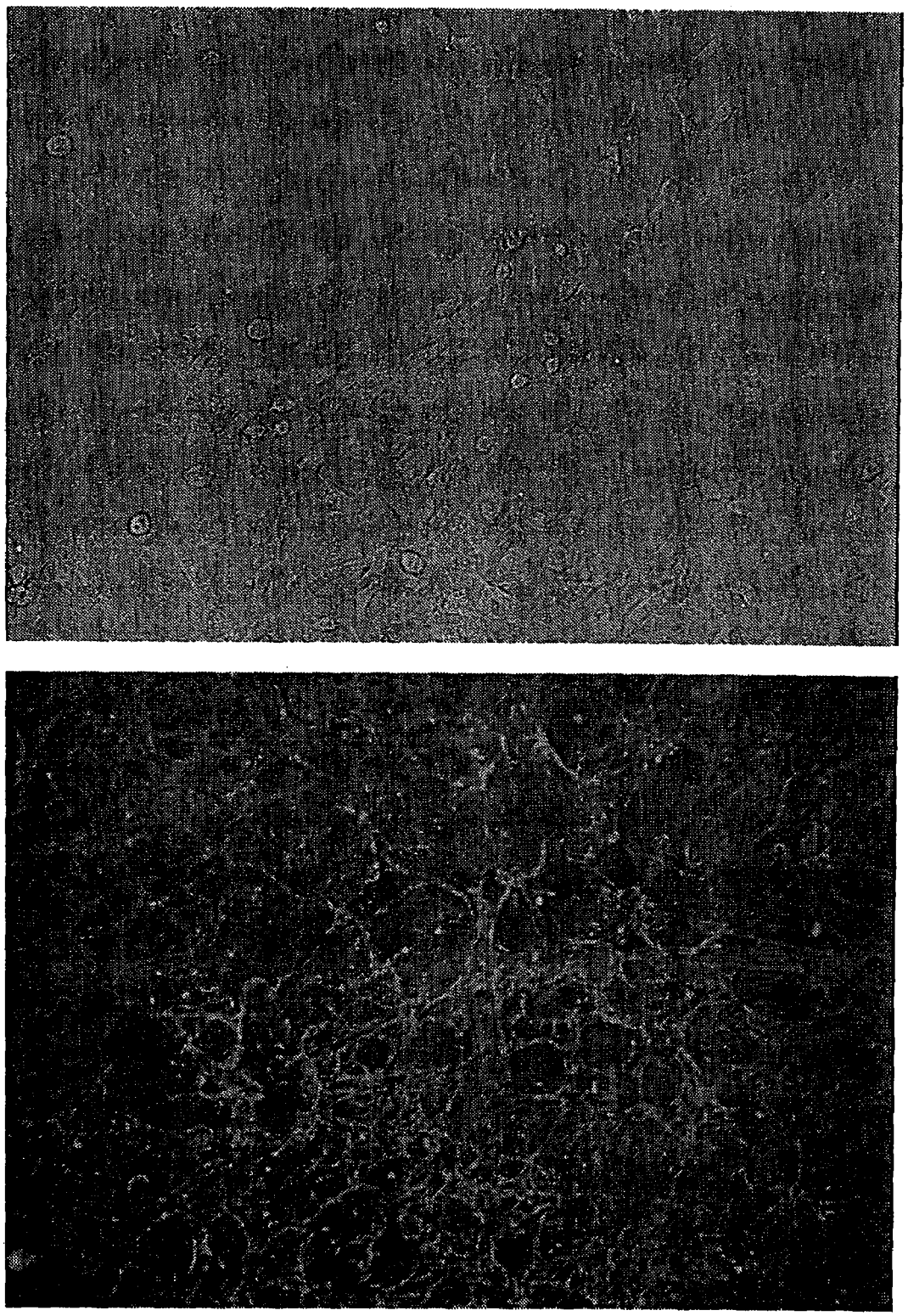
Figure 9. Light microscopic (upper figure) and fluorescence microscopic (bottom figure) picture after transduction with TmHU-GFP.

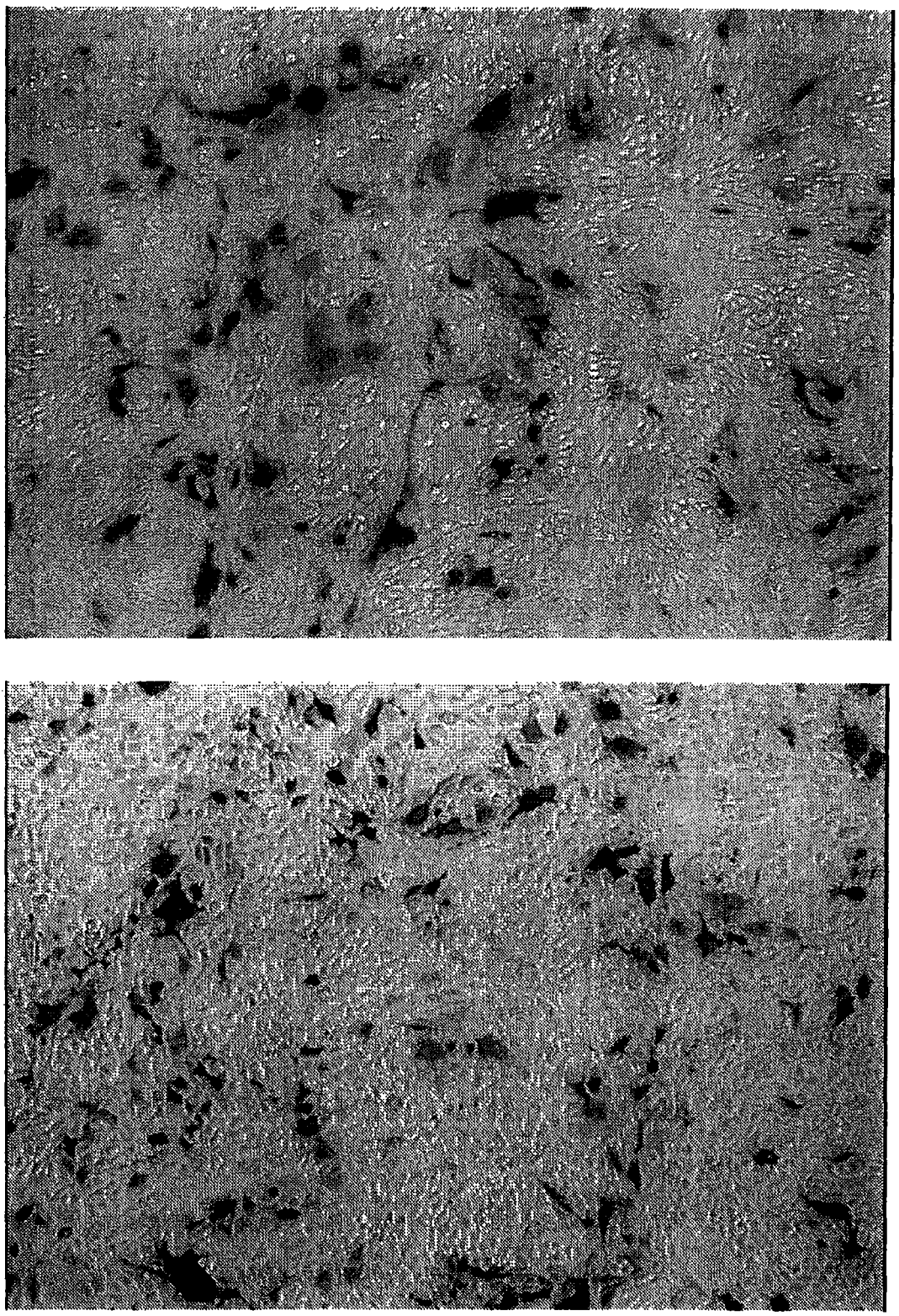
Figure 10. Examples for transfection using liposome-coated TmHU/DNA complexes.

SEQUENCE LISTING

```
<160> NUMBER OF SEQ ID NOS: 10

<210> SEQ ID NO 1
<211> LENGTH: 270
<212> TYPE: DNA
<213> ORGANISM: Thermotoga maritima
<220> FEATURE:
<221> NAME/KEY: CDS
<222> LOCATION: (1)..(270)
<223> OTHER INFORMATION: histone-like HU-protein (TmHU)

<400> SEQUENCE: 1 atg aac aaa aaa gaa ctg atc gac agg gtg gcg aag aaa gca ggt gcg      48
Met Asn Lys Lys Glu Leu Ile Asp Arg Val Ala Lys Lys Ala Gly Ala
 1               5                  10                  15 aag aaa aag gat gta aaa ttg att ctc gac acc atc ctt gaa acg atc      96
Lys Lys Lys Asp Val Lys Leu Ile Leu Asp Thr Ile Leu Glu Thr Ile
             20                  25                  30 aca gaa gct ctc gca aag ggt gaa aag gtt cag atc gtt gga ttc gga     144
Thr Glu Ala Leu Ala Lys Gly Glu Lys Val Gln Ile Val Gly Phe Gly
         35                  40                  45 agc ttc gaa gtg agg aag gcc gct gca aga aaa ggc gtg aat cct cag     192
Ser Phe Glu Val Arg Lys Ala Ala Ala Arg Lys Gly Val Asn Pro Gln
     50                  55                  60 aca aga aaa ccc atc acc att ccc gaa aga aag gtc ccg aag ttc aaa     240
Thr Arg Lys Pro Ile Thr Ile Pro Glu Arg Lys Val Pro Lys Phe Lys
 65                  70                  75                  80 ccc gga aaa gcc ctc aaa gag aag gtc aag                             270
Pro Gly Lys Ala Leu Lys Glu Lys Val Lys
                 85                  90

<210> SEQ ID NO 2
<211> LENGTH: 90
<212> TYPE: PRT
<213> ORGANISM: Thermotoga maritima
```

-continued

<400> SEQUENCE: 2

Met Asn Lys Lys Glu Leu Ile Asp Arg Val Ala Lys Lys Ala Gly Ala
1               5                   10                  15

Lys Lys Lys Asp Val Lys Leu Ile Leu Asp Thr Ile Leu Glu Thr Ile
            20                  25                  30

Thr Glu Ala Leu Ala Lys Gly Glu Lys Val Gln Ile Val Gly Phe Gly
        35                  40                  45

Ser Phe Glu Val Arg Lys Ala Ala Arg Lys Gly Val Asn Pro Gln
    50                  55                  60

Thr Arg Lys Pro Ile Thr Ile Pro Glu Arg Lys Val Pro Lys Phe Lys
65                  70                  75                  80

Pro Gly Lys Ala Leu Lys Glu Lys Val Lys
                85                  90

<210> SEQ ID NO 3
<211> LENGTH: 468
<212> TYPE: DNA
<213> ORGANISM: Artificial Sequence
<220> FEATURE:
<223> OTHER INFORMATION: Description of Artificial Sequence:TmHU-EGF
      fusion protein
<220> FEATURE:
<221> NAME/KEY: CDS
<222> LOCATION: (1)..(468)
<223> OTHER INFORMATION: TmHU-EGF fusion protein
<220> FEATURE:
<221> NAME/KEY: misc_feature
<222> LOCATION: (1)..(267)
<223> OTHER INFORMATION: TmHU portion of TMHU-EGF fusion protein
<220> FEATURE:
<221> NAME/KEY: misc_feature
<222> LOCATION: (289)..(468)
<223> OTHER INFORMATION: epidermal growth factor (EGF) portion of
      TmHU-EGF fusion protein

<400> SEQUENCE: 3 atg aac aaa aaa gaa ctg atc gac agg gtg gcg aag aaa gca ggt gcg      48
Met Asn Lys Lys Glu Leu Ile Asp Arg Val Ala Lys Lys Ala Gly Ala
1               5                   10                  15 aag aaa aag gat gta aaa ttg att ctc gac acc atc ctt gaa acg atc      96
Lys Lys Lys Asp Val Lys Leu Ile Leu Asp Thr Ile Leu Glu Thr Ile
            20                  25                  30 aca gaa gct ctc gca aag ggt gaa aag gtt cag atc gtt gga ttc gga     144
Thr Glu Ala Leu Ala Lys Gly Glu Lys Val Gln Ile Val Gly Phe Gly
        35                  40                  45 agc ttc gaa gtg agg aag gcc gct gca aga aaa ggc gtg aat cct cag     192
Ser Phe Glu Val Arg Lys Ala Ala Ala Arg Lys Gly Val Asn Pro Gln
    50                  55                  60 aca aga aaa ccc atc acc att ccc gaa aga aag gtc ccg aag ttc aaa     240
Thr Arg Lys Pro Ile Thr Ile Pro Glu Arg Lys Val Pro Lys Phe Lys
65                  70                  75                  80 ccc gga aaa gcc ctc aaa gag aag gtc ccg cgg cac tat tcc gta gga     288
Pro Gly Lys Ala Leu Lys Glu Lys Val Pro Arg His Tyr Ser Val Gly
                85                  90                  95 aat agt gac tct gaa tgt ccc ctg tcc cac gat ggg tac tgc ctc cat     336
Asn Ser Asp Ser Glu Cys Pro Leu Ser His Asp Gly Tyr Cys Leu His
                100                 105                 110 gat ggt gtg tgc atg tat att gaa gca ttg gac aag tat gca tgc aac     384
Asp Gly Val Cys Met Tyr Ile Glu Ala Leu Asp Lys Tyr Ala Cys Asn
        115                 120                 125

```
tgt gtt gtt ggc tac atc ggg gag cga tgt cag tac cga gac ctg aag        432
Cys Val Val Gly Tyr Ile Gly Glu Arg Cys Gln Tyr Arg Asp Leu Lys
    130                 135                 140 tgg tgg gaa ctg ggc cac gct ggc cac ggg ccg cgg                        468
Trp Trp Glu Leu Gly His Ala Gly His Gly Pro Arg
145             150                 155

<210> SEQ ID NO 4
<211> LENGTH: 156
<212> TYPE: PRT
<213> ORGANISM: Artificial Sequence
<220> FEATURE:
<223> OTHER INFORMATION: Description of Artificial Sequence:TmHU-EGF
      fusion protein
<220> FEATURE:
<221> NAME/KEY: DOMAIN
<222> LOCATION: (1)..(89)
<223> OTHER INFORMATION: TmHU portion of TMHU-EGF fusion protein
<220> FEATURE:
<221> NAME/KEY: DOMAIN
<222> LOCATION: (97)..(156)
<223> OTHER INFORMATION: epidermal growth factor (EGF) portion of
      TmHU-EGF fusion protein

<400> SEQUENCE: 4

Met Asn Lys Lys Glu Leu Ile Asp Arg Val Ala Lys Lys Ala Gly Ala
 1               5                  10                  15

Lys Lys Lys Asp Val Lys Leu Ile Leu Asp Thr Ile Leu Glu Thr Ile
            20                  25                  30

Thr Glu Ala Leu Ala Lys Gly Glu Lys Val Gln Ile Val Gly Phe Gly
        35                  40                  45

Ser Phe Glu Val Arg Lys Ala Ala Ala Arg Lys Gly Val Asn Pro Gln
    50                  55                  60

Thr Arg Lys Pro Ile Thr Ile Pro Glu Arg Lys Val Pro Lys Phe Lys
65                  70                  75                  80

Pro Gly Lys Ala Leu Lys Glu Lys Val Pro Arg His Tyr Ser Val Gly
                85                  90                  95

Asn Ser Asp Ser Glu Cys Pro Leu Ser His Asp Gly Tyr Cys Leu His
            100                 105                 110

Asp Gly Val Cys Met Tyr Ile Glu Ala Leu Asp Lys Tyr Ala Cys Asn
        115                 120                 125

Cys Val Val Gly Tyr Ile Gly Glu Arg Cys Gln Tyr Arg Asp Leu Lys
    130                 135                 140

Trp Trp Glu Leu Gly His Ala Gly His Gly Pro Arg
145             150                 155

<210> SEQ ID NO 5
<211> LENGTH: 1014
<212> TYPE: DNA
<213> ORGANISM: Artificial Sequence
<220> FEATURE:
<223> OTHER INFORMATION: Description of Artificial Sequence:TmHU-eGFP
      fusion protein
<220> FEATURE:
<221> NAME/KEY: CDS
<222> LOCATION: (1)..(1014)
<223> OTHER INFORMATION: TmHU-eGFP fusion protein
<220> FEATURE:
<221> NAME/KEY: misc_feature
<222> LOCATION: (1)..(267)
<223> OTHER INFORMATION: TmHU portion of TmHU-eGFP fusion protein
<220> FEATURE:
<221> NAME/KEY: misc_feature
<222> LOCATION: (298)..(1014)
<223> OTHER INFORMATION: Aequorea victoria enhanced green fluorescent
      protein (eGFP) portion of TmHU-eGFP fusion protein
```

<400> SEQUENCE: 5

```
atg aac aaa aaa gaa ctg atc gac agg gtg gcg aag aaa gca ggt gcg      48
Met Asn Lys Lys Glu Leu Ile Asp Arg Val Ala Lys Lys Ala Gly Ala
 1               5                  10                  15 aag aaa aag gat gta aaa ttg att ctc gac acc atc ctt gaa acg atc      96
Lys Lys Lys Asp Val Lys Leu Ile Leu Asp Thr Ile Leu Glu Thr Ile
             20                  25                  30 aca gaa gct ctc gca aag ggt gaa aag gtt cag atc gtt gga ttc gga     144
Thr Glu Ala Leu Ala Lys Gly Glu Lys Val Gln Ile Val Gly Phe Gly
         35                  40                  45 agc ttc gaa gtg agg aag gcc gct gca aga aaa ggc gtg aat cct cag     192
Ser Phe Glu Val Arg Lys Ala Ala Ala Arg Lys Gly Val Asn Pro Gln
     50                  55                  60 aca aga aaa ccc atc acc att ccc gaa aga aag gtc ccg aag ttc aaa     240
Thr Arg Lys Pro Ile Thr Ile Pro Glu Arg Lys Val Pro Lys Phe Lys
 65                  70                  75                  80 ccc gga aaa gcc ctc aaa gag aag gtc ccg cgg gcc cgg gat cca ccg     288
Pro Gly Lys Ala Leu Lys Glu Lys Val Pro Arg Ala Arg Asp Pro Pro
                 85                  90                  95 gtc gcc acc atg gtg agc aag ggc gag gag ctg ttc acc ggg gtg gtg     336
Val Ala Thr Met Val Ser Lys Gly Glu Glu Leu Phe Thr Gly Val Val
            100                 105                 110 ccc atc ctg gtc gag ctg gac ggc gac gta aac ggc cac aag ttc agc     384
Pro Ile Leu Val Glu Leu Asp Gly Asp Val Asn Gly His Lys Phe Ser
        115                 120                 125 gtg tcc ggc gag ggc gag ggc gat gcc acc tac ggc aag ctg acc ctg     432
Val Ser Gly Glu Gly Glu Gly Asp Ala Thr Tyr Gly Lys Leu Thr Leu
    130                 135                 140 aag ttc atc tgc acc acc ggc aag ctg ccc gtg ccc tgg ccc acc ctc     480
Lys Phe Ile Cys Thr Thr Gly Lys Leu Pro Val Pro Trp Pro Thr Leu
145                 150                 155                 160 gtg acc acc ctg acc tac ggc gtg cag tgc ttc agc cgc tac ccc gac     528
Val Thr Thr Leu Thr Tyr Gly Val Gln Cys Phe Ser Arg Tyr Pro Asp
                165                 170                 175 cac atg aag cag cac gac ttc ttc aag tcc gcc atg ccc gaa ggc tac     576
His Met Lys Gln His Asp Phe Phe Lys Ser Ala Met Pro Glu Gly Tyr
            180                 185                 190 gtc cag gag cgc acc atc ttc ttc aag gac gac ggc aac tac aag acc     624
Val Gln Glu Arg Thr Ile Phe Phe Lys Asp Asp Gly Asn Tyr Lys Thr
        195                 200                 205 cgc gcc gag gtg aag ttc gag ggc gac acc ctg gtg aac cgc atc gag     672
Arg Ala Glu Val Lys Phe Glu Gly Asp Thr Leu Val Asn Arg Ile Glu
    210                 215                 220 ctg aag ggc atc gac ttc aag gag gac ggc aac atc ctg ggg cac aag     720
Leu Lys Gly Ile Asp Phe Lys Glu Asp Gly Asn Ile Leu Gly His Lys
225                 230                 235                 240 ctg gag tac aac tac aac agc cac aac gtc tat atc atg gcc gac aag     768
Leu Glu Tyr Asn Tyr Asn Ser His Asn Val Tyr Ile Met Ala Asp Lys
                245                 250                 255 cag aag aac ggc atc aag gtg aac ttc aag atc cgc cac aac atc gag     816
Gln Lys Asn Gly Ile Lys Val Asn Phe Lys Ile Arg His Asn Ile Glu
            260                 265                 270 gac ggc agc gtg cag ctc gcc gac cac tac cag cag aac acc ccc atc     864
Asp Gly Ser Val Gln Leu Ala Asp His Tyr Gln Gln Asn Thr Pro Ile
        275                 280                 285 ggc gac ggc ccc gtg ctg ctg ccc gac aac cac tac ctg agc acc cag     912
Gly Asp Gly Pro Val Leu Leu Pro Asp Asn His Tyr Leu Ser Thr Gln
    290                 295                 300
```

```
tcc gcc ctg agc aaa gac ccc aac gag aag cgc gat cac atg gtc ctg    960
Ser Ala Leu Ser Lys Asp Pro Asn Glu Lys Arg Asp His Met Val Leu
305                 310                 315                 320 ctg gag ttc gtg acc gcc gcc ggg atc act ctc ggc atg gac gag ctg   1008
Leu Glu Phe Val Thr Ala Ala Gly Ile Thr Leu Gly Met Asp Glu Leu
                325                 330                 335 tac aag                                                            1014
Tyr Lys

<210> SEQ ID NO 6
<211> LENGTH: 338
<212> TYPE: PRT
<213> ORGANISM: Artificial Sequence
<220> FEATURE:
<223> OTHER INFORMATION: Description of Artificial Sequence:TmHU-eGFP
      fusion protein
<220> FEATURE:
<221> NAME/KEY: DOMAIN
<222> LOCATION: (1)..(89)
<223> OTHER INFORMATION: TmHU portion of TMHU-eGFP fusion protein
<220> FEATURE:
<221> NAME/KEY: DOMAIN
<222> LOCATION: (100)..(338)
<223> OTHER INFORMATION: Aequorea victoria enhanced green fluorescent
      protein (eGFP) portion of TmHU-eGFP fusion protein

<400> SEQUENCE: 6
```

Met Asn Lys Lys Glu Leu Ile Asp Arg Val Ala Lys Lys Gly Ala
 1               5                  10                  15

Lys Lys Lys Asp Val Lys Leu Ile Leu Asp Thr Ile Leu Glu Thr Ile
                20                  25                  30

Thr Glu Ala Leu Ala Lys Gly Glu Lys Val Gln Ile Val Gly Phe Gly
            35                  40                  45

Ser Phe Glu Val Arg Lys Ala Ala Arg Lys Gly Val Asn Pro Gln
        50                  55                  60

Thr Arg Lys Pro Ile Thr Ile Pro Glu Arg Lys Val Pro Lys Phe Lys
65                  70                  75                  80

Pro Gly Lys Ala Leu Lys Glu Lys Val Pro Arg Ala Arg Asp Pro Pro
                85                  90                  95

Val Ala Thr Met Val Ser Lys Gly Glu Glu Leu Phe Thr Gly Val Val
                100                 105                 110

Pro Ile Leu Val Glu Leu Asp Gly Asp Val Asn Gly His Lys Phe Ser
            115                 120                 125

Val Ser Gly Glu Gly Glu Gly Asp Ala Thr Tyr Gly Lys Leu Thr Leu
        130                 135                 140

Lys Phe Ile Cys Thr Thr Gly Lys Leu Pro Val Pro Trp Pro Thr Leu
145                 150                 155                 160

Val Thr Thr Leu Thr Tyr Gly Val Gln Cys Phe Ser Arg Tyr Pro Asp
                165                 170                 175

His Met Lys Gln His Asp Phe Phe Lys Ser Ala Met Pro Glu Gly Tyr
            180                 185                 190

Val Gln Glu Arg Thr Ile Phe Phe Lys Asp Asp Gly Asn Tyr Lys Thr
        195                 200                 205

Arg Ala Glu Val Lys Phe Glu Gly Asp Thr Leu Val Asn Arg Ile Glu
    210                 215                 220

Leu Lys Gly Ile Asp Phe Lys Glu Asp Gly Asn Ile Leu Gly His Lys
225                 230                 235                 240

Leu Glu Tyr Asn Tyr Asn Ser His Asn Val Tyr Ile Met Ala Asp Lys
                245                 250                 255

```
Gln Lys Asn Gly Ile Lys Val Asn Phe Lys Ile Arg His Asn Ile Glu
            260                 265                 270

Asp Gly Ser Val Gln Leu Ala Asp His Tyr Gln Gln Asn Thr Pro Ile
        275                 280                 285

Gly Asp Gly Pro Val Leu Leu Pro Asp Asn His Tyr Leu Ser Thr Gln
    290                 295                 300

Ser Ala Leu Ser Lys Asp Pro Asn Glu Lys Arg Asp His Met Val Leu
305                 310                 315                 320

Leu Glu Phe Val Thr Ala Ala Gly Ile Thr Leu Gly Met Asp Glu Leu
                325                 330                 335

Tyr Lys

<210> SEQ ID NO 7
<211> LENGTH: 90
<212> TYPE: PRT
<213> ORGANISM: Escherichia coli
<220> FEATURE:
<223> OTHER INFORMATION: HU DNA-binding protein, alpha subunit, GenBank
      GI:118256

<400> SEQUENCE: 7

Met Asn Lys Thr Gln Leu Ile Asp Val Ile Ala Glu Lys Ala Glu Leu
1               5                   10                  15

Ser Lys Thr Gln Ala Lys Ala Ala Leu Glu Ser Thr Leu Ala Ala Ile
            20                  25                  30

Thr Glu Ser Leu Lys Glu Gly Asp Ala Val Gln Leu Val Gly Phe Gly
        35                  40                  45

Thr Phe Lys Val Asn His Arg Ala Glu Arg Thr Gly Arg Asn Pro Gln
    50                  55                  60

Thr Gly Lys Glu Ile Lys Ile Ala Ala Ala Asn Val Pro Ala Phe Val
65                  70                  75                  80

Ser Gly Lys Ala Leu Lys Asp Ala Val Lys
                85                  90

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence:nuclear
      translocation sequence

<400> SEQUENCE: 8

Arg Pro Ala Ala Thr Lys Lys Ala Gly Gln Ala Lys Lys Lys
1               5                   10

<210> SEQ ID NO 9
<211> LENGTH: 40
<212> TYPE: DNA
<213> ORGANISM: Artificial Sequence
<220> FEATURE:
<223> OTHER INFORMATION: Description of Artificial Sequence:PCR
      oligonucleotide primer TmHU-N

<400> SEQUENCE: 9
gggggtcata tgaacaaaaa agaactgatc gacagggtgg                          40

<210> SEQ ID NO 10
<211> LENGTH: 37
<212> TYPE: DNA
<213> ORGANISM: Artificial Sequence
```

```
<220> FEATURE:
<223> OTHER INFORMATION: Description of Artificial Sequence:PCR
      oligonucleotide primer TmHU-C

<400> SEQUENCE: 10
ttccggatcc ctatcacttg accttctctt tgagggc                                    37
```

METHOD FOR TRANSFER OF MOLECULAR SUBSTANCES WITH PROKARYOTIC NUCLEIC ACID-BINDING PROTEINS

CROSS-REFERENCES TO RELATED APPLICATIONS

The present application is a continuation of U.S. patent application Ser. No. 10/954,549, filed Sep. 29, 2004, now U.S. Pat. No. 7,435,595, which is a continuation of U.S. patent application Ser. No. 10/129,393, filed Oct. 28, 2002, now abandoned, which is the national stage under 35 U.S.C. §371 of PCT/EP00/10875, filed Nov. 3, 2000, which claims priority to German Patent Application No. 19952983.3, filed Nov. 2, 1999. The contents of U.S. Ser. No. 10/954,549 and 10/129,393 are incorporated herein by reference in their entirety.

BRIEF SUMMARY OF THE INVENTION

The present invention is with respect to a method for the transfer of nucleic acids and/or nucleic acid analogs, and/or nucleic acids and/or nucleic acid analog and/or substances containing amino acids, especially of nucleic acids such as DNA in form of plasmids, into prokaryotic or eukaryotic cells.

FIELD OF THE INVENTION AND STATE OF TECHNOLOGY

Transfection is the introduction of nucleic acids such as nucleotides, antisense RNA, ribozymes, or especially DNA in the form of plasmids, chromosomes, or chromosome fragments for the expression of a gene in cells. The term transfer is here analogous, where in general language usage the term transfection is especially used for gene transfer. Apart from the transfer of nucleic acids, the directed and efficient transfer of additional active substances such as proteins, peptides, therapeutic drugs and other molecular substances is of great interest. The transfer process is of essential significance, both for biomedical basic research and for the pharmaceutical-biotechnological industry. Some proteins, among them therapeutically relevant ones, are only processed correctly during production in eukaryotic cells, since the modification machinery that continues to modify a protein even after the translation is in prokaryotic organisms largely not present or in a significantly different way. Other proteins, in contrast, are advantageously produced in prokaryotic host cells, since here large quantities of the protein can be produced economically and easily. Furthermore, transfection and targeted expression of certain genes is an important tool of cell and molecular biology for the characterization and analysis of biological processes. Transfection of plant cells is an important method for plant technology with respect to the production of plants with new properties and ingredients (transgene plants) or herbicide-resistant plants. Finally, in the framework of biomedical research cells are regularly transfected with single-stranded nucleic acids (ssDNA or ssRNA), or with nucleic acid analogs (e.g., peptide nucleic acids, PNAs), which become intra-cellularly effective as effectors, e.g., as specific inhibitors of protein synthesis through so-called antisense techniques. With all these processes and methods, transfection for the specific introduction of relevant nucleic acids is an important process step.

In the same manner, processes are relevant that can directly transport a protein or peptide into a cell; the most important applications are therapeutics. For instance, intracellular antibodies can be used to recognize specific pathogens in cells and to inhibit them. One method to achieve this is the electroporation of macromolecules into the target cells; however, this method can only be used in vivo and with low efficiency and relatively high losses with respect to the cells (cf. E. J. Verspohl, I. Kaiserling-Buddemeier, A. Wienecke, *Introducing specific antibodies into electro-permeabilized cells is a valuable tool for eliminating specific cell functions*, Cell. Biochem. Funct. Vol. 15, pp. 127-134, 1997).

For the transfer of nucleic acids into cells several methods are known according to the state of technology. Among them are—as with the previously named process for the transfer of proteins—physical processes such as electroporation, where by the connection with an electrical field the membrane of cells is perforated, thus becoming permeable for large macromolecules. However, electroporation is often difficult with sensitive cells and often accompanied with a low survival rate of the cells. In the case of eukaryotic cells, according to the state of technology, chemical methods are most often used, for instance, the coprecipitation of calcium phosphate and DNA or the formation of higher-molecular complexes, for instance, from DEAE-(diethylaminoethyl-)dextrane and DNA (cf. Y. W. Yang & J. C. Yang, "Studies of DEAE-dextran-mediated gene transfer", Biotechnol. Appl. Biochem. 1997, Vol. 25, pp. 47-51) or of dendrimers with DNA (cf. J. F. Kukowska-Latallo, A. U. Bielinska, J. Johnson, R. Spindler, D. A. Tomalia, & J. R. Baker Jr., "Efficient transfer of genetic material into mammalian cells using Starburst polyamidoamine dendrimers", Proc. Natl. Acad. Sci. U.S.A. 1996, Vol. 93, pp. 4897-4902). The basic principle of these transfection reagents is, first, compacting of the long and mechanically rigid nucleic acid threads; such compacting is in most of the cases an important prerequisite for the successful uptake of nucleic acids into the cells. Occasionally, this is achieved by a polycation such as, e.g., pure or modified polylysine (cf., for instance, patent WO 98/06869).

With medical-pharmaceutical applications, liposome-based systems on the basis of cationic lipids are often preferred for transfection; they have the advantage of high efficiencies. Therewith, an inclusion of the nucleic acids in cationic liposomes of various origins and compositions occurs (cf., the commercial products PerFect from Invitrogen, FuGene from Roche, Lipofectamine from Life Technologies, PolyFectin from Biontex, and LipoTaxi from Stratagene). A comprehensive and up-to-date review can be found at R. J. Lee & L. Huang, "Lipidic vector systems for gene transfer", Crit. Rev. Ther. Drug Carrier Syst. 1997, Vol. 14, pp. 173-206. A corresponding large number of international patents exist differing primarily by the formulation of the liposomes used.

However, the named techniques and reagents have their different and individual disadvantages. On the one hand, the existing systems (except for the liposome-based products) are rather inefficient, with yields of only a few percent of the cells being transfected; on the other hand, especially the effective (liposome-based) reagents are increasingly toxic, particularly for sensitive eukaryotic cells. Other disadvantageous properties have also been described, for instance, during the transfection of adherent eukaryotic cells with DEAE-dextrane the only weakly attached cells undesirably separate from their base of the cell culture dish. Also, transfection agents that are not immediately toxic for cells can show properties that influence the cells after transfection. In addition, the existing agents of the new generation such as dendrimers (product SuperFect, Qiagen) are for certain applications only slightly toxic, but rather elaborate in manufacturing and, thus, expensive. Finally, many of the transfection protocols to date require a large number of manipulations by the user and are, thus, complicated and tedious in their use; this can also negatively impact the reproducibility of transfection assays. The standard protocols for transfections mandated by the manufacturers must be modified for each cell type individually and optimized again each time in order to achieve maximum yields. The agents are only suitable for the transport of double-stranded DNA and rarely for single-stranded nucleic acids and practically never for other molecular substances such as, e.g., proteins or peptides. Last but not least, the customary transfection agents each consist of only one or a few molecular species and, therefore, are not very variable in their use.

It is the task of the invention to eliminate or reduce the disadvantages listed above according to the state of technology. Therefore, according to the invention, a method according to claim 1 for the transfer of nucleic acids and/or nucleic acid analogs, and/or nucleic acids and/or nucleic acid analog and/or substances containing amino acids, into prokaryotic or eukaryotic cells is provided, where the nucleic acid or the nucleic acid analog, or the nucleic acids or nucleic acid analogs or substances containing amino acids to be transferred are brought into contact with a prokaryotic nucleic acid-binding protein, in order to form a complex from the nucleic acid, the nucleic acid analog or the nucleic acids or nucleic acid analogs or substances containing amino acids and the nucleic acid-binding protein and subsequently, the complex of nucleic acid, nucleic acid analog and/or nucleic acids or nucleic acid analogs or substances containing amino acids and the prokaryotic nucleic acid-binding protein are brought into contact with the prokaryotic or eukaryotic target cells in order to achieve a transfer of the complex into the cells.

Advantageous application forms of the present invention result from the sub-claims of the description.

DETAILED DESCRIPTION OF THE INVENTION

The present invention concerns a method for the transfer of nucleic acids, nucleic acid analogs, and/or nucleic acids or nucleic acid analog or substances containing amino acids, especially of nucleic acids such as DNA in the form of plasmids into prokaryotic or eukaryotic cells.

To achieve this, a prokaryotic, nucleic acid-binding protein is bound under suitable incubation conditions covalently to the substance to be transferred or by a non-covalent association with the nucleic acid to be transferred, and this complex is added to the target cells. The special character of the prokaryotic nucleic acid-binding protein to the condensation of the DNA favors here the transfer of DNA-based active substances significantly. For the control of the uptake and the increase of the efficiency, the prokaryotic nucleic acid-binding protein can show additional characteristics, for instance, in the form of additional fusions. The cells internalize the complex of protein and active substance, respectively, protein and nucleic acid. Different formats are shown schematically in FIG. 1.

For the transfer, a prokaryotic, nucleic acid-binding protein is used, preferably from a thermostable organism and even more preferably from a hyperthermophilic organism. When nucleic acids are used as substance to be transferred, the nucleic acid-binding protein forms a reversible complex with the nucleic acid; the prokaryotic protein condenses and compacts the nucleic acid. Thus, this complex is protected from undesirable effects, for instance, the degradation by nucleases. Nucleic acid molecules condensed in such a way can be taken up—passively or actively—through the cell membrane of eukaryotic cells or the cell wall of prokaryotic cells into these cells after respective incubation. If a coding gene in the form of a corresponding DNA (for instance, a plasmid) is used as nucleic acid, the gene can subsequently be expressed by the target cell. If, on the other hand, a protein or a peptide is used as molecular substance to be transported, a fusion on the level of gene technology between the protein or peptide to be transferred and the transferring protein is favorable. In order to increase the efficiency, the nucleic acid-binding protein can be combined (fused) with effectors on the basis of proteins or peptides. Furthermore, the use of a protein that shows a typical signature for nuclear translocation in its sequence can be advantageous.

Furthermore, a wrapping of the complex with lipids, polyethylene glycol, or other molecules can be advantageous with respect to increased efficiency and in regard to the biological properties of the complex.

An important feature for the transfection of nucleic acids is their condensation. These molecules normally possess a long inflexible structure that has little flexibility in solution. Due to the comprehensive coding length of genes, the DNA can be very long and thus show physical properties unfavorable for transfection. Condensation, in this invention, is the reduction of the unfavorable length-to-diameter ratio of the DNA by agglomeration of the DNA thread or also a circular plasmid to a compact structure, that is, to a small volume.

Optimal condensation distinguishes itself by the development of an almost globular structure. Condensation of nucleic acids presupposes the presence of condensation agents; here, a customary function of these condensation agents is the compensation of the negative charges on the polyphosphate backbone of the DNA and other nucleic acids.

According to the stipulation of the invention, the prokaryotic nucleic acid-binding protein advantageously stems from a hyperthermophilic organism, that is, an organism that exists at temperatures of more than 75° C. The advantage of proteins from these organisms lies, among others, in the fact that they can be handled very easily due to their special stability properties and, for instance, cooling of the agents during purification and storage is not necessary. Furthermore, proteins from these organisms can be produced and purified easily and with a high yield recombinantly in *Escherichia coli*. Therefore, the high stability of the proteins against denaturation can be used to perform purification under rather stringent conditions, thus avoiding possible contamination in the preparations, for instance, also by bacterial lipopolysaccharides (endotoxins), DNases, proteinases, RNases, among others, limiting it to a minimum below the detection limit of common analytical methods. Helpful in this regard are also the properties of the protein TmHU (*Thermotoga maritima* HU-protein) preferentially used in this invention to be spectroscopically transparent in the wavelength range from 260 to 300 nm; this allows easily a fast and sensitive spectroscopic analysis of contaminations from nucleic acids and other proteins. Preferred for reproducible and efficient transfer rates of nucleic acids, nucleic acid analogs and/or amino acids containing substances, according to the invention, are pure preparations of transfer reagents, since contaminations, especially from bacterial endotoxins but also from proteinases, DNases and RNases, can impair the transfer results. This applies especially to sensitive cells, respectively, for processes with low transfer efficiencies.

Histones are proteins in eukaryotic cell nuclei that bind nucleic acids primarily or entirely unspecifically and whose purpose consists mainly in the compacting (condensation) of DNA, for instance, by charge neutralization and hydrophobic effects, referred by the protein. Thus, they reduce the effective spatial demand of the DNA within the cell nucleus. Histone-like proteins fulfill, according to current knowledge, an analogous task in the simpler structured (without nucleus) prokaryotic organisms. For instance, the DNA-binding protein from the hyperthermophilic organism *Thermotoga maritima* (histone-like protein) is not only superior to those stemming from eukaryotic histones with respect to their stability but also with respect to manageability and the lesser structural complexity. For instance, eukaryotic histones are associates of up to eight different protein sub-units all of which must be produced separately and assembled with DNA in one complex; this is complicated in vitro and elaborate. In the present invention, prokaryotic histone-like proteins, preferably from the HU-protein stemming from the hyperthermophilic organism *Thermotoga maritima*, are used.

The tests conducted by the inventors surprisingly show that this prokaryotic DNA-binding, histone-like protein HU from the hyperthermophilic eubacterium *Thermogata maritima* (species of thermotogales), called TmHU in the following, not only binds, protects, and condenses nucleic acids, but in addition is able to transport these nucleic acids into different cell types extremely effectively. Therewith, the efficiencies of a subsequent gene expression are significantly higher than the comparable established agents without any recognizable signs of cellular toxicity. The transfer protocol is simple, robust and requires a very small effort of time for the execution of the transfer.

In the same manner it could be shown that also amino acid-containing substances, for instance, proteins or peptides, preferably proteins, fused to TmHU were taken up into the target cells by way of the uptake effect of TmHU.

In addition, the circumstance has proven advantageous that the histone-like protein can be produced recombinantly in the bacterium *Escherichia coli* with a very high yield and can be isolated easily and cost-effectively in spectroscopically pure form. The hyperthermophilic origin, for instance, does not require preparation and storage of the protein under cooled conditions. In addition, the primary step of cleaning, the separation of the HU-protein from the mass of the *Escherichia coli*-host proteins, takes place by a simple heat precipitation, where nearly only the thermostable TmHU-protein remains in solution.

It could be shown that the TmHU-protein demonstrates outstanding properties with respect to the transfection of cells. The protein compacts (condenses) nucleic acids to a stable complex. Thus, a perfect protection against degradation of the nucleic acids by nucleases is provided. The complexes are taken up efficiently into cells.

Furthermore, peptides or protein domains in addition can be fused to the TmHU protein by way of gene technology, which gives altered properties to the complexes. Thus, modified TmHU proteins can allow for an increase of uptake efficiency or directed uptake into the cells. For modification, for instance, peptides come into consideration for the binding to cellular surface structures; it is known that peptides with the sequence motive arginine-glycine-aspartate (RGD) bind preferably to the often existing integrins of the type $\alpha_v\beta_3$ or $\alpha_v\beta_5$ at the cell surface. It is known for other peptide motifs that they cause an insertion into eukaryotic cell membranes by their amphipathic structural nature, thus making an uptake of molecules by the cells possible. Finally, the increase of uptake efficiency and a specification of cell types can also be achieved by the usage of proteins or protein domains that bind as effectors to cellular surface receptors. An example of this is the epidermal growth factor EGF that can bind highly specifically to the EGF receptor (overexpressed on some tumor cell types). Thus, the uptake of the TmHU/EGF-DNA-complexes can take place specifically into such tumor cells. But even after the uptake of the complexes in cells, adhering functional domains can contribute to an increase in efficiency.

As an example, proteins that effect an endosome release and peptides for the targeted uptake into eukaryotic cell nuclei by NLS sequences (NLS, nuclear localization signal) can be named.

A wrapping of the protein/nucleic acid complexes for further separation from the environment and, if applicable, for an increase of the transfection efficiency can be achieved by a wrapping with a liposome membrane. Based on the state of technology, liposomes can be easily produced; thereby, a passive inclusion of the protein/nucleic acid complex into the liposomes occurs. These constructs have the advantage of decreased immunogenicity with in vivo use in organisms. Additionally, by amalgamation of the liposome sheath with the cell membrane an increase of cell uptake can occur. An encapsidation of the protein/nucleic acid complexes can also occur by the use of other molecular substances, e.g., by polyethylene glycol of the molecular mass 2000 Da (PEG 2000). According to the state of technology it has already been demonstrated that such a PEGinylation leads to a significant decrease of the immune response on in vivo applications (cf. for instance the summary by M. D. Scott & K. L. Murad, "Cellular camouflage: fooling the immune system with polymers", *Curr. Pharm. Des.* 1998, Vol. 4, pp. 423-438).

The transfer of nucleic acids, nucleic acid analogs and/or amino acids containing substances in cells is demonstrated in each of the following examples with the transfer of coding DNA sequences for the transfection of a reporter gene as well as with the transfer of a protein (GFP) in target cells. For a prokaryotic protein, the HU-protein from *Thermotoga maritima* which has been proven very suitable for the described method is used hereby. The protein has two typical signatures for a nuclear translocation with the transfer of the protein into eukaryotic cells, comparable with the translocation sequence RPAATKKAGQAKKK (SEQ ID NO:8) according to Robbins, Dilworth, Laskey, and Dingwall, *Cell* 64, pp. 615-623, 1991; thus, a nuclear translocation of the protein and of the molecular substances (DNA, proteins) associated with it is assured with a probability of more than 95% (ascertained with the computer program PSORT II used according to the state of technology). Especially for the transfer of DNA in cells does this nucleus translocation have significant meaning for the large efficiency of the method. However, the following example 8 clearly shows that the protein cannot only transfer DNA in cells but also proteins attached to TmHU. Thus, the protein also has the advantageous property to pass eukaryotic cell membranes.

A special advantage of the TmHU protein is its lack of toxicity in the examples listed below and the fact that adherent cells do not become detached from the cell culture containers during transfection. These properties distinguish the protein from other transfection agents such as liposomes or synthetic compounds (dendrimers). At the same time, the property of the TmHU to origin from a hyperthermophilic organism constitutes a special advantage for the use of the system. Thus, the recombinant production is especially simple and a great purity of the protein preparation can be assured. The extremely high thermostability of the protein allows for long and stable storage even under otherwise unfavorable environmental conditions. Especially, it is possible to generate the protein/nucleic acid complexes necessary for the transfection at high temperatures. If DNA is mixed with the TmHU protein in suitable mass ratios and brought to a high temperature (around 90° C.) for a short time from approximately 0.5 to 10 min, a fine precipitate from DNA and TmHU is formed which is especially suitable for high transfection efficiencies. Such a possibility is only available when hyperthermophilic nucleic acid-binding proteins are employed. The incubation of the nucleic acid with the TmHU protein at customary room temperature conditions can range from 0.5 to 180 minutes where an incubation time of 60 minutes is usually sufficient. For the transfer of nucleic acids with TmHU it has proven advantageous to add calcium to the TmHU/DNA-mixture during the production of the complexes which accelerates the complex formation. The incubation of the precipitates formed either at room temperature or at high temperature with the target cells can, depending on cell type and application case, range from 30 seconds to several days. Especially suitable for the present invention are nucleic acid-binding proteins and proteins from thermophilic and especially hyperthermophilic prokaryotic organisms derived from the former. From the domain of the archaea especially the representatives of the Crenarchaeota (hyperthermophilic archaea bacteria) are good candidates together with representatives of the taxonomic groups of the Pyrodictiales, Sulfolobales, Thermoproteales, or the unclassified Crenarchaeota such as *Aeropyrum, Caldococcus, Cenarchaeum, Igneococcus, Pyrolobus, Sulfophobococcus, Thermodiscus*, and *Thermosphaera*. With the euryarchaeota especially the proteins from the taxonomic classes of the Thermococcales and the Thermoplasmales are relevant. But thermophilic and hyperthermophilic eubacteria also have nucleic acid-binding proteins naturally that can be employed within the framework of an application according to the invention; this includes, for instance, the representatives of the taxonomical classes of the thermosulfo-bacteria, the Aquificales, Thermotogales or the group of the *Thermus/Deinococcus* bacteria.

Apart from proteins from hyperthermophilic or thermophilic organisms, proteins from other prokaryotic organisms can also be employed for a successful transfection, as the following example 8 (using the HU-protein from *Escherichia coli*) shows. Here, the efficient formation of the complexes with the prokaryotic protein necessary for the transfection with nucleic acids occurs, preferably by addition of appropriate amounts of calcium to the mixture; a heating step for the production of the fine precipitates must here be relinquished. Thereby, the proteins can be isolated from mesophilic organisms from the kingdom of the archaebacteria or eubacteria or constitute modifications of these natural proteins. As representatives of the archaebacteria, the taxonomic groups of the Corarcheota and the Euryarchaeota can be named, the latter with the families of the Archaeoglobales, Halobacteriales, Methanobacteriales, Methanococcales, Methanomicrobiales, Methanopyrales, Methanosarcinales, Thermococcales, and Thermoplasmales. To the taxonomic groups of the eubacteria, including primarily non-thermophilic or non-hyperthermophilic organisms, in this context belong especially the following groups: the Aquificales, the group of the Chlamydiales/Verrucomicrobia, the group of the Coprothermobacteriae, the Cyanobacteriae, the group of the Cytophageles/green sulfur bacteria, the group Fibrobacteria/Acidobacteria, the Firmicutes, the group of the Flexitipesk, the Fusobacteria, the group of the Holophaga, the group of the Nitrospira, the Planctomycetales, the Proteobacteria, the Spirochaetales, and the group of the Synergistes.

When using prokaryotic organisms as target cells for the described transfer technology the formation of the fine precipitates by short-term heating of the TmHU/DNA-mixture can provide an increase of the transfection efficiency if a protein from a thermophilic or a hyper-thermophilic organism is used. Apart from a transfection that occurs by simple incubation of the TmHU/DNA-complexes with the prokaryotic cells, electroporation according to the state of technology with the help of the TmHU/DNA-complexes can be successful. Thereby, the DNA is protected by the TmHU and stabilized in its structure. With the following example 1 it could be demonstrated that TmHU even in high concentrations is not toxic for *Escherichia coli*. Analogous, a transfer of proteins or other molecular substances in prokaryotic cells can be successfully performed.

At the same time, the TmHU protein protects in vivo nucleic acids from enzymatic degradation. The recombinantly produced protein binds in the bacteria cells to the nucleic acids present there, such as plasmids. On this basis, a system can be manufactured that is suitable for the production of large quantities of nucleic acids of high purity and without the danger of the enzymatic degradation through nucleases, at economic conditions.

An area of application especially important for the transfer of molecular substances in cells is the use of plant cells as target cells. These plant cells distinguish themselves by a sturdy cell wall that can hardly be penetrated, thus, currently hardly any methods are known for the transport of molecular substances such as DNA or proteins in plant cells. However, the extremely stable TmHU/DNA-protein complexes can be suitable, with customary methods according to the state of technology such as chemical transfection, electroporation or even simple incubation of the TmHU/DNA complexes, to achieve a transfer into the plant cells. Thereby, again, the nuclear translocation sequences present in the TmHU play an important role with respect to the achievable high efficiency of the method described in the present invention.

The gene-technological modification of plants, for instance, can provide an essential contribution to the safeguarding of the world food supply by the cultivation of high-yield varieties with better properties. Western Europe has at least a 20% loss through diseases, pests, and weeds. An important application of the invention can therefore also be the transfection of plant cells. However, to date there are only a few very elaborate, insufficient and expensive gene transfer processes known for the transfection of plant cells. The most popular method in this respect is the use of the bacterium *Agrobacterium tumefaciens*, causing tumors at the root collar, in order to bring the DNA into the cells. However, the bacterium only attacks dicotyledonous plants; monocotyledonous, on the other hand (among them important crops), are not transfected. Other, hitherto insufficiently effective and especially elaborate possibilities for gene transfer are electroporation and microinjection. Moreover, the method of particle bombardment ("magic bullets") is used, often successfully but also rather expensive. The use of TmHU and a certain molecular substance can be significantly superior to these transfection methods with respect to efficiency and cost. Thereby, especially modifications of the protein are employed which are for instance able to break down the otherwise impenetrable cell wall of plant cells on a locally limited level by enzymes fused to the TmHU, thus providing a suitable uptake route for the TmHU/DNA-complex. One respective application lies especially in the area of yield increase by the development of higher-yield or more valuable varieties from the standpoint of nutrition physiology (modification or increase of the content of ingredients such as proteins, fatty acids, flavors, or starch); by the avoidance of pest attacks (introduction of resistance genes whose gene product is toxic for the respective pest); by the avoidance of plant diseases as well as the blocking of weed growth (by herbicide resistance genes) and the introduction of foreign DNA for the production of active ingredients inside the plants. This can occur by an application according to the invention of the prokaryotic nucleic acid-binding protein that allows the introduction of the plasmid DNA in plants.

For the molecular (therapeutic) substance to be transported in medical applications, DNA, for instance, can be used that codes for intracellularly or extracellularly effective proteins. The therapeutic DNA can, thereby, be introduced into the cell either single-stranded or double-stranded. Likewise, a coupling of sequence-specific oligonucleotides to the prokaryotic proteins could also be envisioned referring to a specific complex formation with the prokaryotic protein by hybridization with the therapeutic ssDNA; this would substitute the unspecific nucleic acid binding described above with a specific binding. An additional starting point for the transfer of therapeutically active substances would be the complex formation with ribozymes that have a specific recognition sequence for a RNA associated with pathologic conditions. This RNA is catalytically cleaved and deactivated by the binding of the ribozymes.

As an alternative to nucleic acids, a therapy can also be done by proteins or peptides introduced into the cell. For instance, an HIV therapy could be based on trans-dominant (modified) proteins introduced according to the invention, which would then compete with native HIV-proteins in the cell thus inhibiting their function. Likewise, peptides or synthetically modified peptides can inhibit the effect of certain HIV proteins, for instance, of the HIV protease. In addition, proteins or peptides can be fused directly to the prokaryotic protein in such a fashion, that a recognition sequence for HIV protease or a cellular protease lies between therapeutically active substance and prokaryotic transport protein, releasing the protein or peptide intracellularly (and, if applicable, again specifically in infected cells). This would allow for the determination of the specificity of an (therapeutic) effect on certain cell types where the prokaryotic protein used would merely present the transport vehicle for the passage into the cells.

An additional application of the present invention is the use of anti-tumor active substances with malignant diseases. In order to achieve this effect, the produced complexes must contain components that assure the transport of the active substance into tumor tissue. Depending on the type of tumor, this occurs for instance by antibodies built into the active substance/protein-complexes that bind to the tumor antigens which are exclusively or as extensively as possible only present on tumor cells. Solid tumors need sufficient blood supply, thus secreting growth factors that initiate the formation of new blood vessels in tumor tissue. The epithelia cells of new blood vessels increasingly express plasma membrane-bound integrins. These receptors recognize specifically the sequence RGD (arginine-glycine-aspartate) and cause a receptor-mediated endocytosis of RGD-containing ligands. This property can also be utilized to address tumor cells and epithelial tissue connected with it by fusing RGD-exposing peptides to the prokaryotic transport proteins causing an uptake of the therapeutic substance into the tumor tissue. Other tumors show a significantly higher representation of the natural EGF-receptor on the cell surface. In this case the suggestion presents itself to accomplish a specificity of the uptake of the complexes described in the present invention through fusion of the EGF-domain to the prokaryotic transport protein as described in the following example 6. A combination of various receptor binding properties accomplishes, apart from an improved tissue specificity, a therapy that attacks several areas of the tumor simultaneously and reduces the formation of cells resistant to the active substances. For active substances, nucleic acids such as single- and double-stranded DNA or RNA can be employed. The proteins coded on them can, for instance, initiate apoptosis in the cell by engaging at the respective points in the cellular signal transduction cascades. For an expanded tumor specificity and thus greater certainty transcription promoters can be used that are preferably active in tumor cells. In the same manner, peptides can be employed as molecular substances to be transported, which cause an inhibition of the matrix metallo-proteinases. Especially the inhibition of MMP-2 and MMO-9 can show a marked effect by short peptide sequences.

In principle, the invention described here can also be used for the correction of inborn genetic defects such as ADA-deficiency, hemophilia, Duchenne muscular dystrophy, and cystic fibrosis. These diseases are monocausal, i.e., they can be traced to the defect of a single gene. The introduction of this gene in the correct form is, as a rule, sufficient to eliminate the symptoms of the disease or to diminish them. For these applications, a stable gene expression must be achieved either through stable episomal vectors or an integration of the therapeutic DNA into cellular chromosomes. For this, the transferred nucleic acids may contain nucleic acid sequences that make integration easier. For instance, single-stranded DNA can be used carrying at their ends ITR sequences (inverted terminal repeats) of the adeno-associated virus which contribute to the chromosomal integration. In addition, apart from the therapeutic DNA or RNA, a protein can be transported along into the cell, actively serving as a catalyst for the integration, e.g., HIV-integrase or Rep78 and Rep68 of the adeno-associated virus.

Ideally, the expression of correcting genes takes place under the control of the natural promoters assuring at the same time an adapted regulation. A cell type-specific targeting of the complex of DNA and nucleic acid-binding prokaryotic protein is therefore, in many cases, not necessary. For instance, with hemophilia patients the missing factor of the blood clotting cascade can be produced in muscle tissue where the factors are fused with a suitable signal sequence causing them to be secreted from the cell and reaching their active location, the blood stream.

Apart from nucleic acids discussed in the various examples above, proteins or peptides can also be transferred that trigger apoptosis or necrosis. Suitable, for instance, are catalytic domains of bacterial toxins (e.g., diphtheria toxin, cholera toxin, botulism toxin, and others) that inhibit protein biosynthesis in the cell with high efficiency, thus triggering necrosis. Hereby, it can be an advantage that only a few molecules are necessary to kill a cell. Another therapeutic starting point is the transport of the thymidine kinase of the herpes-simplex-virus in tumor cells. This enzyme phosphorylates nucleotide building blocks and thereby show a reduced substrate specificity towards the cellular kinases so that also artificial nucleotides such as Ganciclovir are phosphorylated. During the DNA replication into newly synthesized DNA strands, phosphorylated Ganciclovir is integrated as well and leads to the termination of the replication which, in turn, prevents the cell division.

In many cases of practical application an efficient release of the transported substances within the cell is necessary, i.e., the substance must pass through the endosomal membrane successfully. In the examples enumerated below the endosome release is non-limiting since a gene expression or the transport of a protein (GFP as marker protein, cf. example 7) usually takes place with high efficiency. Should a limitation occur through endosome inclusion of the absorbed complexes, then this function can be performed by hemolysines, especially thiolactivated cytolysines, translocation domains of bacterial toxins, or certain viral proteins such as the adenovirus penton protein that are introduced into the complex to be transferred. In addition, this function can also be assumed by chemical substances such as polycations or dendrimers that become attached to the complexes.

Often it is necessary for in vivo applications to keep the immunogenicity of the absorbed complex as low as possible. The humoral immunogenicity of the complex itself and recognition and elimination by the macrophages can be achieved by a masking with polyethylene glycol or a wrapping with a lipid double layer, as shown in the following example 9. Polyethylene, for instance, can be chemically modified so that it is bound covalently to specific SH-groups. The immunogenity of the therapeutically active substance, i.e., the directly introduced proteins or the proteins transcribed and/or translated, can be reduced with a fusion of 35 to 40 GA-(glycine-alanine)-repetitive sequences. GA-rich sequences occur naturally with the EBNA 1-protein of the human Eppstein-Barr virus and protect the viral protein from a breakdown by the cellular proteasome and a representation on MHC-class I receptors. This protective function can be executed for the various proteins and peptides used within the framework of the present invention.

Apart from nucleic acids, proteins, and peptides, other molecule classes can also be employed for the described method for the transfer of molecular substances in cells of the present invention. Thus, peptide derivatives, peptide antibiotics, proteins with modified side chains such as fluorescent markings, alkylizations, acetylizations, peptide or protein conjugates with carbohydrate-, nucleic acid- or lipid components and analogous modifications can be integrated into the complex in the same manner. Likewise, apart from the customarily used coding (double-stranded) plasmids, also single-stranded DNA, single- or double-stranded RNA, chromosomal DNA or chromosome fragments, antisense RNA, ribozymes, catalytic RNA, nucleotides, synthetic nucleic acids such as peptide nucleic acids (PNA) or hybrids thereof can be coupled with the prokaryotic transport protein, by interaction with the nucleic acid-binding site of the protein or also chemically. They are suitable to be taken up into the cells with high efficiency. As non-nucleic acid-like substances to be transported, especially proteins such as antibodies, antibody-analogous substances, protein domains, glycoproteins, enzymes, peptides, peptide hormones, pharmaceutical active ingredients on amino acid basis, lipoproteins as well as structure proteins come into consideration for applications within the framework of the invention.

The compound of the substance to be transported to the prokaryotic transport protein can be viewed under the aspect of different physical interactions. Thus, a hydrophobic effect can dominate for the complex formation. But other forms of interaction can contribute to the formation of a compound such an ionic interactions, ion-dipole interactions, dipole-dipole interactions, hydrogen bonds, van der Waals forces, or dispersion forces. Finally, apart from the examples for non-covalent compounds listed, a covalent compound of substances to be transported and prokaryotic transport protein can be generated. Thereby, either a fusion on the gene level is performed or a chemically stable atomic bonding between two atoms of the interaction partners is formed.

In summary, the transfer method according to the invention shows the following advantages compared to the state of technology:
- significantly higher efficiency as with existing methods;
- no or only minimal toxicity;
- no or only small immunogenicity with in vivo-applications;
- cost-effective production and storage;
- uncomplicated and quick usability;
- transfer of nucleic acids of any chemical type;
- transfer of other covalent or non-covalent coupled amino acid-containing substances such as proteins or peptides;
- largely no limitation regarding the target cells (for example, the method is equally suitable for eukaryotic animal cells, eukaryotic plant cells and prokaryotic cells);
- possibility of variable composition and additional adherence (fusion) of effectors or the wrapping and additional possibilities for the integration of further favorable properties for the cell uptake.

The following examples show applications of this invention, however, they are not meant to limit the protective scope of the invention.

The description and the examples refer to the following figures.

BRIEF DESCRIPTION OF THE DRAWINGS

FIG. 1 shows a schematic overview of possible application methods of the invention with the transport of nucleic acids. The TmHU-protein (Y) refers a condensation of the linear or circular nucleic acid. The protein/nucleic acid complex is then taken up by cells (left figure). For an additional format, for instance, a receptor-referred uptake (middle figure) or a wrapping of the protein/nucleic acid complex can take place (right figure).

FIG. 2 shows a SDS PAGE for the analytics of the purification of TmHU which is produced recombinantly in *Escherichia coli*. Lane 1 shows the soluble portion of the cell extract of *E. coli*. Lane 2 shows the supernatant after the heat precipitation. Lane 3 shows the molecular mass standard (magnitude is listed on the left in the figure). Lane 4 shows the eluate after purification from a cation exchange column. The protein can be obtained with very high purity by uncomplicated and few purification steps.

FIG. 3 shows the spectroscopic characterization of native and purified TmHU. The UV-absorption spectrum of the protein (concentration of 0.5 mg/ml) shows no absorption at 280 or 260 nm that would lead to the conclusion of contamination through foreign proteins or nucleic acids, the preparation, therefore, is very pure. The protein does not show any tyrosine or tryptophane residues and is, thus, spectroscopically transparent in the specified UV range. The three phenylalanine residues of the protein subunits show—as can be expected—a minute absorption at 257 nm.

FIG. 4 shows the measurement of the TmHU compound to the DNA fragments of varying size with the help of the surface plasmon resonance. (●), 56 bp dsDNA-fragment, and (-), calculated Hill-equation with a $K_D$ of 73 nM and a Hill-coefficient of 7.6. (○), 23 bp dsDNA-fragments, and (---), calculated Hill-equation with a $K_D$ of 73 nM and a Hill-coefficient of 1.3. The binding of the protein to the DNA is comparatively strong and with DNA-fragments of common size (>>23 bp) highly cooperative.

FIG. 5 shows the protection of a model DNA before breakdown by nucleases. Various concentrations of different condensation agents were used. Lane 1, size standard. Lane 2-4, TMHU (0.3, 3, and 15 μg); lane 5-7, histones (0.3, 3, and 30 μg); lane 8, size standard; lane 9-11, CTAB (5, 10, and 100 μM); lane 12-14, spermidine (10, 100, and 2000 μM). Under the very stringent requirement unprotected DNA is completely broken down, CTAB and spermidine provide, thereby, hardly any protection against this breakdown. Histones provide a slightly better protection and TmHU provides in this comparison the best protection against breakdown.

FIG. 6 shows the transfection efficiency of TmHU with different cell lines in comparison to standard methods (DEAE-dextrane transfection). Left, transfection of human 293T-cells with TmHU; the transfection efficiency is here approximately 50%. Center, transfection of murine NIH3T3 cells with TmHU; the transfection efficiency is here approximately 30%. Right, transfection of murine NIH3T3 cells with DEAE-dextrane; the transfection efficiency is here approximately up to 10%.

FIG. 7 shows the transfer efficiency of TmHU with NIH 3T3 cells with the protocol described in example 5. Hereby, two different sections of a cell culture cavity are shown; the microscopic magnification at the objective is 20.times. The yield at transfection events amounts here approximately to 2500 positive cells per µg of DNA used.

FIG. 8 shows Western blots for the proof of uptake of the TmHU-EGF-fusion protein in human A431 cells that express the EGF-receptor as tumor markers on the cell surface. Left figure: Western-blot of proteins from the cell lysate after incubation and uptake of the TmHU-EGF fusion protein. Lane 1, transfection with TmHU-EGF; lane 2, transfection with TmHU-EGF/DNA-complex; lane 3, lysate of untransformed A431-cells for the control of the specificity of the anti-EGF-antibody; lane 4, Tm1HU-EGF-fusion protein (standard); lane 5, marking of the molecular mass standard. Right figure: time course of the disappearance of TmHU-EGF from the cell supernatant in the course of the transfection; proof by Western blot. Lanes 1 through 7: incubation with DNA with the transfection; Lanes A through G: incubation without DNA with the transfection. Lane 1, TmHU-EGF comparison standard; lane 2, 0 min., lane 3, 30 min., lane 4, 60 min., lane 5, 90 min., lane 6, 120 min., lane 7, 7 hrs., lane A, 0 min., lane B, 30 min., lane C, 60 min., lane D, 90 min., lane E, 120 min., lane F, 7 hrs. The uptake of the TmHU into the cells can be clearly observed where by the formation of the TmHU-DNA complexes a more efficient uptake is achieved than without this complex formation.

FIG. 9 shows a phase-contrast image (top) and a micrograph under fluorescent light conditions (bottom) of a section from a transfected culture dish of NIH 3T3-cells. The cells were incubated for 5 hours in the medium and then washed with PBS. The green fluorescent cells contain the TmHU-GFP-fusion protein that has been taken up into the cells through the TmHU uptake mechanism.

FIG. 10 shows, by way of example, two cell cultures with NIH 3T3 cells that have been transfected with liposome-wrapped TmHU/DNA complexes. In both sediments a large quantity of positive transformed cells can be registered which express the reporter gene, thus showing a blue color in the test assay.

EXAMPLES

Example 1

Cloning, Recombinant Expression in *Escherichia Coli* and Purification of the Protein HU from *Thermotoga maritima*

According to the state of technology the heterologous expression of a cloned DNA sequence in a prokaryotic host cell is known. By a polymerase-chain reaction (PCR) with the oligonucleotide primers TmHU-N (5'-GGG GGT CAT ATG AAC AAA AAA GAA CTG ATC GAC AGG GTG G-3'; SEQ ID NO:9) and TmHU-C (5'-TTC CGG ATC CCT ATC ACT TGA CCT TCT CTT TGA GGG C-3': SEQ ID NO:10) on genomic DNA from the organism *Thermotoga maritima* a 300 bp-fragment can be amplified and cloned into the prokaryotic expression vector pET11a (Novagen) with standard technology (see Sambrook et al., Molecular Cloning. A Laboratory Manual", 1989, Cold Spring Harbor Laboratory Press). After transformation of the plasmid in *E. coli*-cells of the group BL21 (DE3) (Stratagene) and selection of ampicillin-resistant LB-agar plates a preparatory culture of LB-medium containing 100 µg/ml ampicillin is inoculated with a single colony and shaken over night at 37° C. This preparatory culture is diluted at a ratio of 1:100 into the main culture consisting of the same media type. The main culture is incubated in the shaking incubator at 37° C. until the absorption of the bacteria suspension reaches the value 1.0 at a wavelength of 600 nm. The expression of the *Thermotoga maritima* HU-Gene (TmHU) is subsequently induced by addition of 1 mM isopropyl thiogalactoside (IPTG).

After centrifugation for the separation of the soluble from the insoluble components (50,000 g, 1 hr., 4° C.) the supernatant is heated for 20 min. to 80° C. Thereby, the major part of the host proteins is thermically denatured and settles after cooling as insoluble precipitate. The thermostable protein TmHU presents itself after repeated centrifugation at 50,000 g in enriched and already nearly pure form in the supernatant (FIG. 2).

In the subsequent final purification step the supernatant is further purified by a cation exchange chromatography through a column of the type Poros HS (Perseptive Biosystems). Under the conditions of the resuspension buffer TmHU binds strongly to the cation exchange column. After application of a linear salt gradient of 300 to 2000 mM NaCl TmHU can be eluated separately through chromatography from the still remaining contaminations. FIG. 2 shows the efficiency of the individual purification steps with the help of an 18% SDS-polyacrylamide gel. By the method presented here the TmHU, present under native conditions as dimer, can be obtained in spectroscopically pure form (>95% purity; FIG. 3) with a yield of approximately 20 mg per liter *E. coli*-culture (with simple cultivation method).

Example 2

Proof of the Nucleic Acid-Binding Properties of TmHU

A 56 bp-DNA fragment as well as a 23 bp fragment are amplified with PCR-technology by 2 primers each from which one each is biotinylated, and the resulting double-stranded DNA immobilized at Streptavidin chips. By surface plasmon resonance (SPR) determined by a BIACore unit (Amersham Pharmacia Biotech), the compound of TMHU to the respective immobilized DNA can be measured directly (FIG. 4).

Thereby, TmHU in various concentrations in a buffer containing 50 mM sodium phosphate, pH 7.5 and 100 mM sodium chloride is injected into the flow cell of the DNA chips and the SPR signal is recorded. The plateaus of the signals are directly proportional to the bound quantity to TMHU. An application of the SPR signal against the concentration of the employed TmHU results in a sigmoid curve according to the Hill equation (FIG. 4), which, in the case of the 56 bp-fragment, is characteristic for a highly cooperative compound. The transition center point of the curves, by definition the dissociation constant $K_D$ thereby lies in both cases at a TmHU protein concentration of 73 nM.

Example 3

Protection of Nucleic Acids Against Degradation by Nucleases

1 µg of a circular plasmid DNA (pEGFP-N1, Clontech) in 120 µl sample buffer (20 mM HEPES, pH 7.2, 100 mM NaCl, 5% glycerol, 10 mM MgCl.sub.2) are mixed with TmHU, human histones (Sigma), cetyl-trimethyl-ammonium-bromide (CTAB, Amresco) or Spermidin (Sigma) in three different concentrations each, incubated for one hour at room temperature and subsequently 5 units Benzonase (Merck) were added. After 30 min. incubation at room temperature the samples are brought to concentrations of 0.5% SDS, 20 mM EDTA, the nucleic acids are extracted with phenol/chloroform and precipitated from the aqueous phase with the help of ethanol. Subsequently, after labeling the DNA with the sensitive dye SYBR Gold (Molecular Probes) on a 1% agarose gel the protection of the nucleic acids from nuclease breakdown is analyzed (FIG. 5). In this example the considerable protection of the DNA by TmHU against the degradation by nucleases becomes apparent. The lower molecular substances (CTAB and Spermidin) provide only a poor protection against nuclease degradation; this protection is markedly improved with eukaryotic histones (FIG. 5). However, only with the use of the prokaryotic TMHU protein at otherwise identical test conditions a marked protection of the nucleic acid against nuclease degradation is achieved. Unprotected DNA is completely degraded under the test conditions.

The protection against nuclease-induced degradation is important for the optimization of transfer efficiencies, since in the serum-containing medium and partially also in the target cells the nucleic acids are exposed to a degradation by nucleases. This example further makes clear that the prokaryotic protein, in this respect, is significantly superior to the eukaryotic histones, presumably due to the lack of repetitive structures in the nucleo-histone complexes, characteristic for the eukaryotes, which can favor a cleavage at the binding sites. This protection against degradation is a very favorable characteristic for the method described in the present invention. Thereby, this protection can also be employed in the production of plasmids in vivo to achieve a better production, for instance, in bacteria.

Example 4

Transfection of Eukaryotic Cells

300 µl of a TmHU-solution (0.5 mg/ml) and 6 µl plasmid-DNA (24 µg pCMV-β, coded for the marker protein β-galactosidase) are incubated together for one hour at room temperature. Subsequently, this mix is brought into the medium of semi-confluent murine NIH 3T3- or human 293T-cells (60 mm cell culture dish). The dishes are waved slightly and incubated for 2 days at 37° C. and 5% $CO_2$; during this time no additional medium change is performed. Thereby, a precipitate is formed from protein and nucleic acids that sediment onto the adherent cells. The protein/nucleic acid complex is taken up by the cells during this time. After 48 hours a labeling of the transformed cells with a substrate for the β-galactosidase, 5-bromo-4-chloro-3-indolyl-β-D-galactopyranosid (X-Gal), is performed and the ratio of the labelled (transfected) to the non-labelled (non-transfected) cells is determined. From this the transfection efficiency is calculated.

To this effect, in addition control transfections are performed in which either the nucleic acids or the TmHU, respectively, are missing in the transfection mix (negative control). For a comparison for the determination of the effectiveness an optimized transfection with DEAE dextrane (Mammalian Transfection Kit, Stratagene) is performed in parallel according to the instructions of the manufacturer (positive control). The negative controls show—as was expected—in each case no labelled cells, therefore no transfections. With the positive control (DEAE/dextran-transfection) a maximum of 10% of the cells in the culture dish are labelled (see FIG. 6); this is within the scope of magnitudes for these efficiencies for this method known from literature. A transfection of the 293T cells with the DEAE dextrane method is not successful since the only weakly adhering cells will become detached by the transfection method. In contrast, a transfection with TmHU for both cell lines is possible without problems; a detachment of the 293T-cells cannot be observed. In case of the TmHU-based transfections the transfection efficiencies amount to 30% each (murine NIH3T3 cells), respectively 50% (human 293T cells). Consequently, a clear increase of the transfection efficiencies of the cells when compared with a standard system can be observed (see FIG. 6). It seems possible to further increase these yields by optimizations. Up to the fixation of the cells (killing) for the labeling with X-Gal, a negative influence of the TmHU transfection on the survival and the growth of the cells could not be observed; consequently, TmHU is not toxic for the cells.

Example 5

Alternative Protocol for the Transfection of Eukaryotic Cells

100 µl of a TmHU solution (0.5 mg/ml) in phosphate buffer, pH 7.0, and 11 of a plasmid-DNA solution (4 µg pCMV-β, coding for the marker protein β-galactosidase), are mixed with 10 µl of a 20 mM $CaCl_2$-solution and heated for 40 min. to 95° C. After cooling to room temperature and incubation for an additional 20 min., 350 µl DMEM-medium with 10% FBS is added to the mixture and placed into the cavity of a 12-well-plate, into which 50,000 NIH 3T3-cells have been seeded 16 hours earlier. Prior to the addition the medium above the cells is removed. After a slight waving, the dish is incubated in the incubator for 12 hrs. at 37° C. and 5% $CO_2$ The medium is then exchanged for 1 ml fresh complete culture media, (DMEM with 10% FBS) and the cells incubated for an additional 36 hrs. Now the test for β-galactosidase-expression described in example 4 is performed and the cells are counted with the help of the grid ocular. Typically, with this method 10,000 positive cells can be obtained per well (examples in FIG. 7). If the protocol described is carried out without the addition of TmHU to the transfection mixture (control for efficiency of a standard calcium phosphate transfection for comparison), the yield is approximately 10 transformed cells, a factor of $10.\text{sup}.3$ less yield. The yield of transfection events in the present example with approximately 2500 positive cells per µg DNA is approximately 5- to 10 times higher than that of a DEAE-dextran-transfection (roughly 300 to 400 transfection events per µg DNA).

Example 6

Use of Modified Proteins with the Example of TmHU-EGF

TmHU-EGF is a fusion protein from TmHU and the human epidermal growth factor (EGF) that shall facilitate tan uptake into EGF-receptor carrying target cells as, for instance, the human A431 cells used here (cf. E. J. Meuillet et al., "Sialidase gene transfection enhances epidermal growth factor receptor activity in an epidermoid carcinoma cell line, A431"; Cancer Res. 1999, Vol. 59, pp. 234-240). The fusion protein is produced after cloning by SacII-restriction sites into the pET11a expression vector named in example 1 in accordance with the standard method described in example 1. 100 µl TmHU-EGF (0.5 mg/ml) are incubated for 1 hour with 8 µg of the pCMV-β-plasmids and the resulting complex of TmHU-EGF/DNA brought into the medium of semi-confluent A431-cells according to the directions of example 4. As a control, 100 µl TmHU-EGF without additional DNA is brought onto identically treated cells. In a negative control, in addition, a semi-confluent cell culture dish is prepared into which no TmHU-EGF is given.

The cells are incubated for 2 hours each on ice, then washed with cold PBS-buffer and then incubated at 37° C. for 45 min. The medium over the cells is removed and trypsin/EDTA-solution for the separation of the not yet internalized complex and of the adherent cells is added. The trypsin digestion is stopped by the addition of FCS-containing medium (fetal calf serum) and the resuspended cells are washed three times with cold PBS buffer. After the last washing step the cells are resuspended in 100 µl PBS-buffer and then mixed with 100 µl 4% SDS and 2 mM PMSF, rigorously mixed and immediately heated for 10 min. to 95° C. The cell lysates thus obtained are applied to a 15% SDS polyacrylamide gel and analyzed according to the electrophoresis by Western blot (initial antibodies: rabbit polyclonal anti-EGF, Santa Cruz; Secondary antibodies: goat anti-rabbit IgG, HRP-conjugate, BioRad).

In the specific Western blot (FIG. 8, left) the protein can be verified as specific bands in the lysates that have been incubated with the TmHU-EGF chimera, in the lysates without TmHU-EGF incubation, however, these bands are absent. This shows that the protein TmHU-EGF is internalized into the A431-cells and that this absorption is verifiable through specific Western blot. This absorption is independent from the presence of DNA in the experiment, however, the absorption is more efficient in the presence of DNA, this is supported by a second experiment that is carried out in analogy to the transfection experiment described above (cf. FIG. 8, right). Here, the uptake of the TmHU-EGF chimera into the A431 target cells is detected by the decline of the TmHU quantity in the medium over the cells. Here, too, is becomes apparent that DNA-loaded TmHU-EGF is significantly faster removed from the cell residue than in the control experiment without DNA.

Example 7

Use of Modified Proteins with the Example of TmHU-GFP

TmHU-GFP is a fusion protein of TmHU and the green fluorescent protein of the deep sea jellyfish *Aequorea victoria*, which shows the remarkable characteristic of green fluorescence, without cofactor, that is, only on the basis of its tertiary structure. Fusion constructs with GFP often retain this fluorescence of the native protein. In the present example, the GFP is fused C-terminally to the TmHU with a linker peptide. The fusion is carried out on the DNA level; using gene-technological standard methods, the GFP gene together with the linker, hereby, was cut out of the vector pEGFP-N1 of Clontech and inserted at the 3' end of the TmHU gene. The purification of TmHU-GFP takes place in analogy to that of the TMHU in example 1, by a cation exchange chromatography. The fusion protein can be purified in solution with high yield.

TMHU-GFP possesses, just a GFP itself, a greenish fluorescence. Likewise, the DNA-compound of the fusion protein remains intact, since if high molecular DNA is added to the protein solution and subsequently centrifugated, the TmHU-GFP with the DNA is coprecipitated and shows greenish lightning complexes. Therefore, it can be assumed that both parts of the fusion construct remain functionally intact. This is an additional evidence to the fact that the system can easily be modified on the genetic level and that the structure of TmHU presents a stable framework for the creation of further variants in form of fusion constructs.

With the present variant TmHU-GFP absorption studies can now be conducted in eukaryotic cells in vivo, that is, without fixation of the cells. To this effect, a 2 cm culture dish with NIH 3T3-cells is rinsed with PBS-buffer and then 50 µl TmHU-GFP-solution (0.1 mg/ml) in PBS buffer is added. After a short waving the dishes are incubated for 5 hours at 37° C. and with 5% $CO_2$ and subsequently, after rinsing three times with PBS photos of the GFP-fluorescence are taken with a fluorescence microscope and digital camera. In FIG. 9, one can clearly see the outlines of the cells in the fluorescence (below) and in comparison a phase contrast exposure (top) of the same segment. These results point to the fact that the fusion construct is taken up into the cells with great efficiency and that hereby not the individual vesicles such as lysosomes are concentrated and accumulated but that the fusion protein is present in the entire cytosol.

It is known from literature that this property of the cell absorption is not caused by the GFP; it must, therefore, have been referred through the TmHU-portion of the fusion construct.

The example therefore demonstrates that prokaryotic histone-like proteins such as TmHU are taken up with great efficiency into cells and thereby do not accumulate in the lysosomes but spread in the cytosol. This absorption property can explain the high gene transfer efficiency of TmHU. Thereby, the efficient absorption in cells as well as the potential release from endosomes and other cellular compartments contribute to the high transfection efficiency. In addition, the example demonstrates that proteins attached to or fused with TmHU (for instance, also therapeutically relevant proteins) can be introduced with high efficiency through TmHU into eukaryotic cells. Hereby, TmHU works as a transport vehicle for the fusion protein for the traversing of the cell membrane.

Example 8

Transfection with HU from *Escherichia coli* (EcoHU)

100 µl of a EcoHU-solution (HU-protein from *Escherichia coli*), 0.5 mg/ml, are mixed with 1 µl plasmid-solution (4 mg/ml, coding for β-galactosidase) and heated for 40 min. to 95° C. and then incubated for 20 min. at room temperature. The mixture is elutriated in 350 µl DMEM and 10% FBS with 1% PS and subsequently applied onto NIH 3T3 cells (50 000 cells in a cavity of a 12 well plate). After 2 days the cell culture is examined for expression of β-galactosidase. Under these conditions, 104 cells show β-galactosidase-expression. This is a significantly smaller yield as in the case of the analogous use of TmHU (roughly 600 positive transformed cells). The example demonstrates that a transfection under the conditions set in the present invention is principally also possible with histone-like proteins of other bacteria, in this case, of a mesophilic bacterium.)

Example 9

Packaging of the TmHU-DNA-Complex in Liposomes and Transfections with these Liposome-TmHU-DNA-Complexes One of the newer methods for gene transfer into eukaryotic cells consists of packaging the DNA into cationic lipid vesicles which then fuse with the cell membrane and, in this manner, introduce the DNA into the cell. However, these results in smaller yields than could initially be expected after the efficient absorption into the cells, because often these lipid vesicles accumulate in the endosomes and a transfer of the DNA into the cytoplasm does not take place and, subsequently, transport into the cell nucleus. In this example it is examined whether the liposome-referred and TmHU-referred transfections can be combined synergistically.

First, a transfection with the reagent Tfx-50 (Promega) was conducted according to manufacturer's specifications. Hereby, a charge ratio of positive charges (lipid) to negative charges (DNA) of 2:1 was the most efficient (optimization according to manufacturer's specifications). With the method, 80% of the confluent seeded NIH 3T3-cells were transfected with 1 μg plasmid-DNA (pCMV-β), 3 μl Tfx-50-reagent and 200 μl DMEM. After an incubation of one hour 1 ml full-medium (DMEM with 10% FBS) is added. On average, 3 300 positive (transformed) cells per μg DNA were obtained. This transfection efficiency is in the same order of magnitude as the optimized TmHU transfection (cf example 5).

In the next step, the transfection was performed with the addition of different quantities of TmHU with varying lipid quantity. The highest transfection results were achieved by a one-hour incubation of 1 μg DNA with 12.5 μl TmHU-solution (0.5 mg/ml) and a charge ratio of 4:1 (regarding Lipid:DNA), (4.5 μl lipid suspension, 12.5 μl TmHU-solution, and 1 μg DNA on 200 μl of the transfection solution). The quantity of the positive cells per μg of employed DNA increases at this point to an average of 16 000 transformed cells. The yield of a combined TmHU-lipofection is, thus, approximately five to six times higher than the optimized protocols of the lipofection as well as of the TmHU-transfection alone. Two examples for this type of transformed cells are shown in FIG. 10.

Although is cannot be ruled out that in this experiment TmHU-referred transfection and lipofection occur parallel to each other, in each case, a clearly more synergistic effect can be noted, because the efficiency is significantly higher than the sum of the respective individual contributions (especially since less than optimal working conditions are present for the named experiment with respect to the standpoint of the lipofection as well as from the standpoint of the TmHU-transfection). The most probable explanation for the high efficiency is therefore that the generated TmHU-DNA complexes are, at least in part, enclosed into the generated liposomes of the lipofection agent. This wrapping of the TmHU-DNA-complex with a liposome membrane also shows a clearly higher efficiency than compared to the standard methods such as the DEAE-dextane transfection.

The invention claimed is:

1. Method for transferring a nucleic acid, a nucleic acid analog, or a substance containing amino acids into prokaryotic or eukaryotic target cells, comprising the steps of:

(1) contacting the nucleic acid or the nucleic acid analog or the substance containing amino acids to be transferred with a prokaryotic HU-protein or HU-protein modified by fusion with a protein, a peptide, or a protein domain, thereby forming a complex of the nucleic acid or the nucleic acid analog or the substance containing amino acids and the prokaryotic HU-protein or the modified HU-protein, and (2) subsequently contacting the complex with the prokaryotic or eukaryotic target cells, thereby transferring the complex into the cells.

2. Method according to claim 1, wherein the nucleic acid is single-stranded or double-stranded DNA, single-stranded or double-stranded RNA, DNA in the form of plasmids, chromosome fragments, antisense RNA, ribozymes, catalytic RNA, nucleotides, chromosomal DNA or coding mRNA.

3. Method according to claim 1, wherein the nucleic acid is a DNA with a coding sequence for expression in the target cells.

4. Method according to claim 1, wherein the nucleic acid is compacted and protected against degradation by being brought into contact with the prokaryotic HU-protein or the modified HU-protein.

5. Method according to claim 1, wherein the complex of the nucleic acid or nucleic acid analog and the prokaryotic HU-protein or the modified HU-protein is reversible.

6. Method according to claim 1, wherein the prokaryotic HU-protein is from cryophilic, mesophilic, thermophilic, or hyperthermophilic organisms.

7. Method according to claim 1, wherein the procaryotic HU-protein is TmHU (*Thermotoga maritima* HU-protein), Sso7d (from *Sulfolobus solfataricus* and *Sulfolobus acidocaldarius*), Ssh7 (from *Sulfolobus shibatae*), Sac7d (from *Sulfolobus solfataricus* and *Sulfolobus acidocaldarius*), BstHU (from *Bacillus stearothermophilus*), HU (from *Escherichia coli*), IHF (from *Escherichia coli*), BsuHU (from *Bacillus subtilis*), SaHU (from *Sulfolobus acidocaldarius*), BbuHU (from *Borrelia burgdorferi*), BgaHU (from *Borrelia garinii*), BafHU (from *Borrelia afzelii*), IHF (from *Pseudomonas aeruginosa*), DNA-binding protein (*Chlamydia* spp.), Hsa (from *Staphylococcus aureus*), R1HU (from *Rhizobium leguminosarum*), HS1 (from *Streptomyces lividans*), HCj (from *Campylobacter jejuni*), HU (from *Bacillus caldolyticus*), HU (from *Bacillus caldotenax*), HU (from *Bacillus globigii*), HCc (from *Caulobacter crescentus*), DNA-binding protein (from *Deinococcus radiodurans*), HSa (from *Sulfolobus acidocaldarius*), histone-like, DNA-binding protein (from *Streptococcus gordonii*), histone-like, DNA-binding protein (from *Streptococcus mutans*), histone-like, DNA-binding protein (from *Streptococcus pyogenes*), histone-like, DNA-binding protein (from *Streptococcus thermophilus*), histone-like, DNA-binding protein (from *Haemophilus influenzae* Rd), histone-like, DNA-binding protein (from *Listeria monocytogenes*), histone-like, DNA-binding protein (from *Serratia marcescens*), histone-like, DNA-binding protein (from *Salmonella typhimurium*), histone-like, DNA-binding protein (from *Thermus aquaticus*), histone-like, DNA-binding protein (from *Rhizobium meliloti*), histone-like, DNA-binding protein (from *Pseudomonas putida*), histone-like, DNA-binding protein (from *Mycobacterium tuberculosis*), histone-like, DNA-binding protein (from *Mycobacterium leprae*), histone-like, DNA-binding protein (from *Zymomonas mobilis*), histone-like, DNA-binding protein (from *Yersinia pseudotuberculosis*), histone-like, DNA-binding protein (from *Mycobacterium bovis*), histone-like, DNA-binding protein (from *Mycoplasma hyopneumoniae*), histone-like, DNA-binding protein (from *Mycobacterium smegmatis*), histone-like, DNA-binding protein (from *Helicobacter pylori*), histone-like, DNA-binding protein (from *Aquifex aeolicus*), histone-like, DNA-binding protein (from *Agrobacterium tumefaciens*), histone-like, DNA-binding protein (from *Pseudomonas aeruginosa*), histone-like, DNA-binding protein (from *Helicobacter pylori*), histone-like, DNA-binding protein (from *Xanthomonas campestris*), histone-like, DNA-binding protein (from *Vibrio proteolyticus*), histone-like, DNA-binding protein (from *Streptomyces lividans*), histone-like, DNA-binding protein (from *Rickettsia prowazekii*), histone-like, DNA-binding protein (from *Streptomyces coelicolor*), histone-like, DNA-binding protein (from *Mycoplasma capricolum*), histone-like, DNA-binding protein (from *Borrelia burgdorferi*), histone-like, DNA-binding protein (from *Borrelia japonica*), histone-like, DNA-binding protein (from *Borrelia andersonii*), or HTa (from *Thermoplasma acidophilum*).

8. Method according to claim 1, wherein the modified prokaryotic HU-protein permits the complex to bind to a receptor molecule on the surface of the target cells.

* * * * *